United States Patent [19]
DesMarais et al.

[11] Patent Number: 6,013,589
[45] Date of Patent: *Jan. 11, 2000

[54] ABSORBENT MATERIALS FOR DISTRIBUTING AQUEOUS LIQUIDS

[75] Inventors: Thomas Allen DesMarais; John Collins Dyer, both of Cincinnati, Ohio; Gianfranco Palumbo, Bad Homburg; Bruno Johannes Ehrnsperger, Frankfurt am Main, both of Germany

[73] Assignee: The Procter & Gamble Company, Cincinnati, Ohio

[ * ] Notice: This patent is subject to a terminal disclaimer.

[21] Appl. No.: 09/042,418

[22] Filed: Mar. 13, 1998

[51] Int. Cl.$^7$ ............................... A61F 13/15; C08J 9/28
[52] U.S. Cl. ........................... 442/370; 442/373; 521/62; 521/64; 604/358
[58] Field of Search ..................................... 442/370, 373; 521/62–64, 146, 149, 150; 604/358

[56] References Cited

U.S. PATENT DOCUMENTS

| | | | |
|---|---|---|---|
| 3,255,127 | 6/1966 | von Bonin et al. | 260/2.5 |
| 3,256,219 | 6/1966 | Will | 260/2.5 |
| 3,431,911 | 3/1969 | Meisel, Jr. | 128/287 |
| 3,563,243 | 2/1971 | Lindquist | 128/287 |
| 3,565,817 | 2/1971 | Lissant | 252/312 |

(List continued on next page.)

FOREIGN PATENT DOCUMENTS

| | | | |
|---|---|---|---|
| 0 017 671 A1 | 10/1980 | European Pat. Off. | C08J 9/14 |
| 0 017 672 A1 | 10/1980 | European Pat. Off. | C08J 9/00 |
| 0 049 768 A1 | 4/1982 | European Pat. Off. | C08J 9/00 |
| 0 068 830 A1 | 1/1983 | European Pat. Off. | A61L 15/00 |
| 0 299 762 | 1/1989 | European Pat. Off. | C08F 2/32 |
| 0 480 379 A2 | 4/1992 | European Pat. Off. | C08G 59/50 |
| 1340520 | 9/1963 | France . | |
| 3 109 929 A1 | 1/1982 | Germany | C08J 9/12 |
| 2-239863 | 9/1990 | Japan | A61F 13/15 |
| 2-289608 | 11/1990 | Japan | C08G 18/48 |
| 3-49759 | 3/1991 | Japan | A61F 13/15 |
| 1 493 356 | 11/1977 | United Kingdom | C08J 9/28 |
| 2 188 055 | 9/1987 | United Kingdom | C08G 18/14 |
| WO 94/28839 | 12/1994 | WIPO | A61F 13/15 |

OTHER PUBLICATIONS

Lissant et al., "Structure of High Internal Phase Ratio Emulsions", Journal of Colloid & Interface Science, vol. 47, No. 2, pp 416–423, (May 1974).

Lissant et al., "A Study of Medium and High Internal Phase Ratio Water/Polymer Emulsions", Journal of Colloid & Interface Science, vol. 42, No. 1, pp. 201–108, (Jan. 1973).

Lissant, K.J., "The Geometry of High–Internal–Phase Ratio Emulsions", Journal of Colloid & Interface Science, vol. 22, No. 5, pp. 462–468, (Nov. 1966).

Aubert et al., "Low Density, Microcellular Polystyrene Foams", Polymer, V 26, pp. 2047–2054, (Dec. 1985).

LeMay, J.D., "Mechanical Structure Property Relationships of Micorcellular, Low Density Foams", Mat. Res. Soc. Symp. Proc., vol. 207, pp. 21–26, (Dec. 1991).

Weber et al., "New Melamine–based Elastic Foam", Kunststoffe German Plastics, pp. 843–848, (Nov. 1985).

Young et al., "Preparation of Multishell ICF Target Plastic Foam Cushion Materials by Thermally Induced Phase Inversion Processes", J. Vac. Sci. Technol., vol. 20, No. 4, pp. 1094–2004, (Apr. 1982).

(List continued on next page.)

*Primary Examiner*—Blaine Copenheaver
*Attorney, Agent, or Firm*—Carl J. Roof; Kevin D. Hogg; Jacobus C. Rasser

[57] ABSTRACT

Disclosed are materials capable of distributing and releasing aqueous fluids, e.g., urine, to a storage material, and absorbent articles comprising such fluid distribution materials. These fluid distribution materials have A) a ratio of capillary desorption height (i.e., height at 50% capacity) to capillary absorption height (i.e., height at 50% capacity) of not more than about 1.8:1; B) a capillary desorption height of not more than about 50 cm; C) the ability to wick synthetic urine at 31° C. to a height of 15 cm in not more than about 25 minutes; and D) a vertical wicking capacity at 15 cm of at least about 6 g/g.

38 Claims, 5 Drawing Sheets

U.S. PATENT DOCUMENTS

| | | | |
|---|---|---|---|
| 3,640,753 | 2/1972 | Krauch et al. | 117/62.2 |
| 3,734,867 | 5/1973 | Will | 260/2.5 R |
| 3,763,056 | 10/1973 | Will | 260/2.5 L |
| 3,778,390 | 12/1973 | Ulrich, Jr. | 260/2.5 AN |
| 3,806,474 | 4/1974 | Blair | 260/2.5 AG |
| 3,988,508 | 10/1976 | Lissant | 526/344 |
| 3,993,074 | 11/1976 | Murray et al. | 128/286 |
| 3,994,298 | 11/1976 | DesMarais | 128/285 |
| 4,029,100 | 6/1977 | Karami | 128/284 |
| 4,049,592 | 9/1977 | Marans et al. | 260/2.5 AD |
| 4,061,145 | 12/1977 | DesMarais | 128/275 |
| 4,067,832 | 1/1978 | DesMarais | 260/2.5 AB |
| 4,093,570 | 6/1978 | Miyake et al. | 260/2.5 B |
| 4,110,276 | 8/1978 | DesMarais | 521/123 |
| 4,132,839 | 1/1979 | Marans et al. | 521/159 |
| 4,229,549 | 10/1980 | Usami et al. | 525/76 |
| 4,262,052 | 4/1981 | Kannan et al. | 428/306 |
| 4,283,499 | 8/1981 | Howell | 521/38 |
| 4,376,440 | 3/1983 | Whitehead et al. | 604/387 |
| 4,394,930 | 7/1983 | Korpman | 220/444 |
| 4,425,130 | 1/1984 | DesMarais | 604/389 |
| 4,443,568 | 4/1984 | Woo | 523/406 |
| 4,460,748 | 7/1984 | Rauer | 525/256 |
| 4,473,611 | 9/1984 | Haq | 428/198 |
| 4,522,953 | 6/1985 | Barby et al. | 521/64 |
| 4,536,521 | 8/1985 | Haq | 521/146 |
| 4,540,717 | 9/1985 | Mahnke et al. | 521/52 |
| 4,554,297 | 11/1985 | Dabi | 521/178 |
| 4,603,069 | 7/1986 | Haq et al. | 428/76 |
| 4,606,958 | 8/1986 | Haq et al. | 428/68 |
| 4,611,014 | 9/1986 | Jones et al. | 521/146 |
| 4,612,334 | 9/1986 | Jones et al. | 521/146 |
| 4,613,543 | 9/1986 | Dabi | 428/304.4 |
| 4,634,729 | 1/1987 | Pavlin et al. | 524/285 |
| 4,657,973 | 4/1987 | Endo et al. | 525/67 |
| 4,694,042 | 9/1987 | McKee et al. | 525/66 |
| 4,709,084 | 11/1987 | Pavlin et al. | 560/118 |
| 4,724,242 | 2/1988 | Vassileff | 521/83 |
| 4,725,628 | 2/1988 | Garvey et al. | 521/137 |
| 4,731,391 | 3/1988 | Garvey | 521/137 |
| 4,740,528 | 4/1988 | Garvey et al. | 521/128 |
| 4,775,655 | 10/1988 | Edwards et al. | 502/416 |
| 4,788,225 | 11/1988 | Edwards et al. | 521/147 |
| 4,791,184 | 12/1988 | Nagai et al. | 526/323.2 |
| 4,797,310 | 1/1989 | Barby et al. | 428/71 |
| 4,818,785 | 4/1989 | Otawa et al. | 524/576 |
| 4,839,395 | 6/1989 | Masamizu et al. | 521/56 |
| 4,957,810 | 9/1990 | Eleouet et al. | 428/306.6 |
| 4,959,341 | 9/1990 | Wallach | 502/404 |
| 4,961,982 | 10/1990 | Taylor | 428/41 |
| 4,966,919 | 10/1990 | Williams, Jr. et al. | 521/54 |
| 4,972,002 | 11/1990 | Volkert | 521/120 |
| 4,973,610 | 11/1990 | Hahn et al. | 521/89 |
| 4,987,467 | 1/1991 | Kelly et al. | 521/52 |
| 4,990,541 | 2/1991 | Nielsen et al. | 521/70 |
| 5,006,415 | 4/1991 | Matsumaru et al. | 428/522 |
| 5,006,592 | 4/1991 | Oshima et al. | 524/504 |
| 5,021,462 | 6/1991 | Elmes et al. | 521/63 |
| 5,034,424 | 7/1991 | Wenning et al. | 521/109.1 |
| 5,037,859 | 8/1991 | Williams, Jr. et al. | 521/55 |
| 5,047,225 | 9/1991 | Kong | 423/447.2 |
| 5,051,484 | 9/1991 | Sasaki et al. | 526/151 |
| 5,065,752 | 11/1991 | Sessions et al. | 128/156 |
| 5,066,784 | 11/1991 | Sherrington et al. | 530/334 |
| 5,093,426 | 3/1992 | Sakabe et al. | 525/223 |
| 5,116,880 | 5/1992 | Tokiwa et al. | 521/134 |
| 5,116,883 | 5/1992 | LeMay | 521/178 |
| 5,128,382 | 7/1992 | Elliott, Jr. et al. | 521/178 |
| 5,135,981 | 8/1992 | Matsumaru et al. | 524/547 |
| 5,147,345 | 9/1992 | Young et al. | 604/378 |
| 5,149,720 | 9/1992 | DesMarais et al. | 521/63 |
| 5,200,433 | 4/1993 | Beshouri | 521/64 |
| 5,200,469 | 4/1993 | Hous | 525/245 |
| 5,210,104 | 5/1993 | Bass et al. | 521/64 |
| 5,210,108 | 5/1993 | Spinu et al. | 521/182 |
| 5,221,726 | 6/1993 | Dabi et al. | 528/93 |
| 5,250,579 | 10/1993 | Smits et al. | 521/98 |
| 5,252,619 | 10/1993 | Brownscombe et al. | 521/64 |
| 5,260,345 | 11/1993 | DesMarais et al. | 521/148 |
| 5,276,067 | 1/1994 | Doerge | 521/131 |
| 5,290,820 | 3/1994 | Brownscombe et al. | 521/64 |
| 5,292,777 | 3/1994 | DesMarais et al. | 521/64 |
| 5,318,554 | 6/1994 | Young et al. | 604/378 |
| 5,336,695 | 8/1994 | Nass et al. | 521/109.1 |
| 5,352,711 | 10/1994 | DesMarais | 521/149 |
| 5,369,137 | 11/1994 | Paquet et al. | 521/146 |
| 5,387,207 | 2/1995 | Dyer et al. | 604/369 |
| 5,397,316 | 3/1995 | LaVon et al. | 604/369 |
| 5,500,451 | 3/1996 | Goldman et al. | 521/64 |
| 5,550,167 | 8/1996 | DesMarais | 521/50 |
| 5,563,179 | 10/1996 | Stone et al. | 521/64 |
| 5,633,291 | 5/1997 | DesMarais et al. | 521/64 |
| 5,650,222 | 7/1997 | DesMarais et al. | 442/370 |
| 5,767,168 | 6/1998 | Dyer et al. | 521/149 |
| 5,770,634 | 6/1998 | DesMarais et al. | 521/64 |
| 5,817,704 | 10/1998 | Shiveley et al. | 521/63 |
| 5,827,253 | 10/1998 | Young et al. | 604/369 |
| 5,827,909 | 10/1998 | DesMarais | 523/346 |

OTHER PUBLICATIONS

Gibson et al., "The Mechanics of Foams: Basic Results" and "The Mechanics of Foams: Refinements", Cellular Solids Structure & Properties, Chpts 5 & 6, pp. 120–200, (Dec. 1988).

Aerogels, Jochen Fricke, pp. 92–97. (no date).

Bhumgara, B., "Polymeric Foam Materials on Filtration Media", Filtration and Separation (Mar. 1995), p. 245–251.

Williams, J.W., "High Internal Phase Water–In–Oil Emulsions: Influence of Surfactants and Cosurfactants on Emulsion Stability and Foam Quality", Langmuir, vol. 7, No. 7, pp. 1370–1377 (Jan. 1991).

Kong, F–M., et al. "Summary Abstract: Low–density polystyrene foam materials for direct–drive last inertial confinement fusion targets", J. Vac. Sci. Tech. A., vol. 6, No. 3, pp. 1894–1895 (May/Jun. 1988).

Hainey, P., et al., "Synthesis and Ultrastructural Studies of Styrene–Divinylbenzene Polyhipe Polymers", Macromolecules, vol. 24, No. 1 pp. 117–121 (Dec. 1991).

Avar, et al., "Integral Skin Foams and RIM Materials", Polyurethane Handbook, $2^{nd}$ ed., G. Oerterl Ed., Hanser Publishers, New York, Chapter 7, pp. 329–386 (Dec. 1993).

Curtain et al., "Polymer Foam Cell Growth in Microgravity", J. Cell. Plas., vol. 28, No. 6, pp. 536–556 (Nov./Dec. 1992).

LeMay et al., "Low–Density Microcellular Materials", MRS Bulletin, vol. XV, No. 12, pp. 19–45 (Dec. 1990).

Woods, G., "igh Density and Flexible Foams and Microcellular Elastomers", The ICI Polyurethanes Book, Polyurethane and J. Wiley & Sons Publishers, Chpt. 5, pp. 85–100 (Dec. 1987).

Low Density Cellular Plastics: Physical Basis of Behaviour, Hilyard/Cunningham, Ed., Chapman & Hall, Pub., Fig. 1.3, p. 6 (Dec. 1994).

Low Density Cellular Plastics: Physical Basis of Behaviour, Hilyard/Cunningham, Ed., Chapman & Hall, Pub., Fig. 3.3, p. 59 (Dec. 1994).

Handbook of Plastic Foams: Types, Properties, Manufacture and Applications, A. H. Landrock, Ed., Noyes Pub., Fig. 10, p. 57 (Dec. 1995).

Handbook of Plastic Foams: Types, Properties, Manufacture and Applications, A. H. Landrock, Ed., Noyes Pub., p. 64–65 (Dec. 1995).

Letts, S.A., et al., "Summary Abstract: Characterization of Low–density Foam Materials for Direct–drive Laser Inertial Confinement Fusion Targets", J. Vac. Sci. Technol. A., vol. 6, No. 3, pp. 1896–1897 (May/Jun. 1988).

ABSORBENT MATERIALS FOR DISTRIBUTING AQUEOUS LIQUIDS

TECHNICAL FIELD OF THE INVENTION

This application relates to materials suitable for use in articles suitable for absorbing body liquids. The application particularly relates to materials capable of distributing aqueous liquids (e.g., urine, menses, etc.) and preferably releasing such liquids to liquid storage materials.

BACKGROUND OF THE INVENTION

The development of highly absorbent articles for use as disposable diapers, adult incontinence pads and briefs, and catamenial products such as sanitary napkins is the subject of substantial commercial interest. The ability to provide high performance absorbent articles such as diapers has been contingent on the ability to develop relatively absorbent cores or structures that can acquire, distribute and store large quantities of discharged body liquids, in particular urine. These three functions can be accommodated by specific portions of the absorbent articles optimized for each. An acquisition material (or layer) is designed to take in liquid rapidly during a gush. The gush liquid is stabilized prior to being given up to the contiguous distribution material. The distribution material (or layer) has sufficient capillary pressure (described in more detail below) to pull liquid away from the acquisition member and distribute it throughout the absorbent article, often against the force of gravity to a height of 10–20 cm according to the size of the core. The storage member (or layer) has the highest capillary pressure and may contain hydrogel-forming absorbent polymers (HFAPs) to pull the liquid away from the distribution layer and store the liquid "permanently" away from the skin of the wearer.

Significant effort has been devoted towards the development of superior liquid acquisition and storage components. For example, U.S. Pat. No. 4,898,642 (Moore et al.) issued Feb. 6, 1990, U.S. Pat. No. 4,888,093 (Dean et al.) issued Dec. 19, 1989, U.S. Pat. No. 5,137,537 (Herron et al.), U.S. Pat. No. 5,217,445 (Young et al.), issued Jun. 8, 1993, and U.S. Pat. No. 4,822,453 (Dean et al.) describe curly, stiffened fibers that, when formed into low density webs, do not collapse when wet and retain their ability to acquire liquids at high rates as is experienced in a "gush" situation during urine voiding. Certain types of polymeric foams have been used in absorbent articles for the purpose of actually imbibing, wicking and/or retaining aqueous body liquids. See, for example, U.S. Pat. No. 3,563,243 (Lindquist), issued Feb. 6, 1971 (absorbent pad for diapers and the like where the primary absorbent is a hydrophilic polyurethane foam sheet); U.S. Pat. No. 4,554,297 (Dabi), issued Nov. 19, 1985 (body liquid absorbing cellular polymers that can be used in diapers or catamenial products); U.S. Pat. No. 4,740,520 (Garvey et al.), issued Apr. 26, 1988 (absorbent composite structure such as diapers, feminine care products and the like that contain sponge absorbents made from certain types of super-wicking, crosslinked polyurethane foams). U.S. Pat. No. 5,563,179 (Stone et al.) issued Oct. 8, 1996, describes hydrophilic absorbent foams useful for acquiring and distributing aqueous liquids in, e.g., absorbent cores. Similarly, various nonwoven materials have been proposed for liquid acquisition. Of key importance is the ability of these materials to acquire liquids repeatedly in use, to survive storage in a compressed state, and to release the acquired liquid to a subsequent liquid distribution or storage material.

The art is replete with examples of storage materials, such as "hydrocolloids" or "hydrogel-forming absorbent polymers" or superabsorbent polymers, summarized in "Water-Absorbent Polymers: A Patent Survey", Po, R. *J. M. S.—Rev. Macromol. Chem. Phys.* 1994, C34(4), 607–662. Such storage materials are usually blended with a fibrous web in varying proportions for use in absorbent cores. Other known storage materials include various hydrophilic foams, such as the emulsion-derived foams described in U.S. Pat. No. 5,387,207 (Dyer et al.) issued Feb. 7, 1995.

Comparatively much less development has been described in the literature regarding suitable distribution materials. Often, absorbent core designs contain no specific distribution material at all. Alternatively, the distribution function is combined with either the storage or acquisition function (as in U.S. Pat. No. 5,563,179, supra), which can result in somewhat compromised performance. Poor distribution with an absorbent core used, e.g., in a diaper can result in the accumulation of the acquired liquid in a relatively small part of the absorbent core, generally the crotch area. Here the aforementioned hydrocolloid or hydrogel-forming absorbent polymer ("HFAP") can convert the liquid into a gel. This has several undesirable effects even though the design is widely practiced in the art. Firstly, the accumulation of that volume of liquid in one area tends to distend the product, e.g., by extending the leg gathers in the case of a diaper, resulting in gaps between the product and the legs through which urine can leak. Secondly, the volume of liquid can be uncomfortable for the wearer. Thirdly, this concentration of urine can lead to undesirable effects on the skin which can result in localized dermatitis. Finally, this can also result in premature "gel blocking", as described in U.S. Pat. No. 5,599,335 (Goldman et al.), issued Feb. 4, 1997, with resultant inefficient utilization of the HFAP present in the product.

Effective distribution layers must be able to wick liquid vertically against the force of gravity to function properly in an absorbent core such as is found in a diaper. Vertical wicking capability derives primarily from the surface area per unit volume of the structure and its surface hydrophilicity. This can be measured as capillary absorption height (referred to herein as "CAH", defined infra). The CAH must be sufficient to acquire the aqueous liquids from any acquisition material used for temporary storage and wick the liquid to the remainder of the absorbent core, portions of which may be elevated 20 cm or more relative to the site of liquid insult by the wearer.

Another important property of a liquid distribution material is the ability to give up liquid to the storage components. This can be measured as capillary desorption height (referred to herein as "CDH", defined infra), which is always greater than the CAH. Classically, the CDH is at least about twice the CAH, the difference being referred to as capillary hysteresis.

Yet another important property is wicking speed. The distribution material must be able to wick the aqueous liquid to the height required within a reasonable period of time. In general, this time requirement is established by the rate or repeat insult of additional aqueous liquid in the loading zone. The distribution material should partition the aqueous liquid from the acquisition layer, wick the liquid to a required height, and partition the liquid to the storage layer substantially before the next insult occurs. A further requirement is that the material wick a sufficient volume of liquid so as to have a liquid flux adequate to substantially move the liquid out of the acquisition layer prior to the next liquid insult.

Yet another important property is amount of fluid that the material will absorb (on a g fluid per g material basis). Of particular note is the amount of fluid the material will absorb at a specific height (e.g., 15 cm) in the capillary sorption experiment. The distribution material ideally is able to absorb and move relatively large amounts of fluid per gram of material within the product.

The combination of sufficient CAH (for the height of the product), small CDH, and high wicking speed and flux has not been achieved with prior materials known in the art. Fiber webs can have good wicking speeds but are deficient in liquid flux because of their inherent low capacity (or free absorbent capacity) (due to the relatively high density or insufficient void volume). Thus, they cannot wick enough liquid over time to be adequate. Further, wherein a CAH of >10 cm is needed, these fiber webs must be densified to provide the CAH needed, further reducing liquid flux (and void volume).

If made appropriately, open-celled hydrophilic polymeric foams can provide features of capillary liquid distribution required for use in high performance absorbent cores. Absorbent articles containing such foams can possess desirable wet integrity, can provide suitable fit throughout the entire period the article is worn, and can minimize changes in shape during use (e.g., uncontrolled swelling, bunching). In addition, absorbent articles containing such foam structures can be easier to manufacture on a commercial scale. For example, absorbent diaper cores can simply be stamped out from continuous foam sheets and can be designed to have considerably greater integrity and uniformity than absorbent fibrous webs. Such foams can also be prepared in any desired shape, or even formed into single-piece diapers.

Particularly suitable absorbent foams for absorbent products such as diapers have been made from High Internal Phase Emulsions (hereafter referred to as "HIPE"). See, for example, U.S. Pat. No. 5,260,345 (DesMarais et al.), issued Nov. 9, 1993 and U.S. Pat. No. 5,268,224 (DesMarais et al.), issued Dec. 7, 1993, both of which are incorporated herein by reference. These absorbent HIPE foams provide desirable liquid handling properties, including: (a) relatively good wicking and liquid distribution characteristics to transport the imbibed urine or other body liquid away from the initial impingement zone and into the unused balance of the foam structure to allow for subsequent gushes of liquid to be accommodated; and (b) a relatively high storage capacity with a relatively high liquid capacity under load, i.e. under compressive forces. These HIPE absorbent foams are also sufficiently flexible and soft so as to provide a high degree of comfort to the wearer of the absorbent article; some can be made relatively thin until subsequently wetted by the absorbed body liquid. See also U.S. Pat. No. 5,147,345 (Young et al.), issued Sep.15, 1992 and U.S. Pat. No. 5,318,554 (Young et al.), issued Jun. 7, 1994, which discloses absorbent cores having a liquid acquisition/distribution component that can be a hydrophilic, flexible, open-celled foam such as a melamine-formaldehyde foam (e.g., BASOTECT made by BASF), and a liquid storage/redistribution component that is a HIPE-based absorbent foam.

While these foam-based acquisition/distribution components afford rapid liquid acquisition and relatively efficient distribution and partitioning of liquid to other components of the absorbent core having higher absorption pressures, these foams are nevertheless compromise materials intended to accomplish at least two separate functions. Specifically, the microstructural morphology and mechanical strength of these materials has been optimized to meet two needs, rather than being specifically designed for only one purpose within the absorbent core.

Accordingly, it would be desirable to provide a material that: (1) is specifically designed as an efficient distribution component in an absorbent core; (2) exhibits reduced hysteresis as reflected by a low CDH:CAH ratio; (3) has a relatively low CDH value to allow other core components (e.g., storage components) having higher absorption pressures than the desorption pressure of the distribution foam to partition away liquid; (4) wicks liquid away from the acquisition zone of the absorbent core before the next liquid insult occurs; (5) is soft, flexible and comfortable to the wearer of the absorbent article; and (6) has a relatively high capacity for liquid so as to provide diapers and other absorbent articles that efficiently utilize core components.

SUMMARY OF THE INVENTION

In one respect, the present invention relates to materials that are capable of distributing aqueous liquids, especially discharged body liquids such as urine, menses, etc. These materials have:

A) a ratio of capillary desorption height (i.e., height at 50% capacity) to capillary absorption height (i.e., height at 50% capacity) of not more than about 1.8:1;

B) a capillary desorption height of not more than about 50 cm;

C) the ability to wick synthetic urine at 31° C. to a height of 15 cm in not more than about 25 minutes; and D) a vertical wicking capacity at 15 cm of at least about 6 g/g.

In another respect, the invention relates to absorbent articles comprising a material of the present invention. Such absorbent articles, which are especially suitable for absorbing and retaining aqueous body liquids, comprise:

I) a backing sheet; and

II) an absorbent core associated with the backing sheet such that the absorbent core is positioned between the backing sheet and the liquid discharge region of the wearer of the article, the absorbent core comprising a material of the present invention that is capable of distributing aqueous liquids.

DETAILED DESCRIPTION OF THE INVENTION

Figure 1:
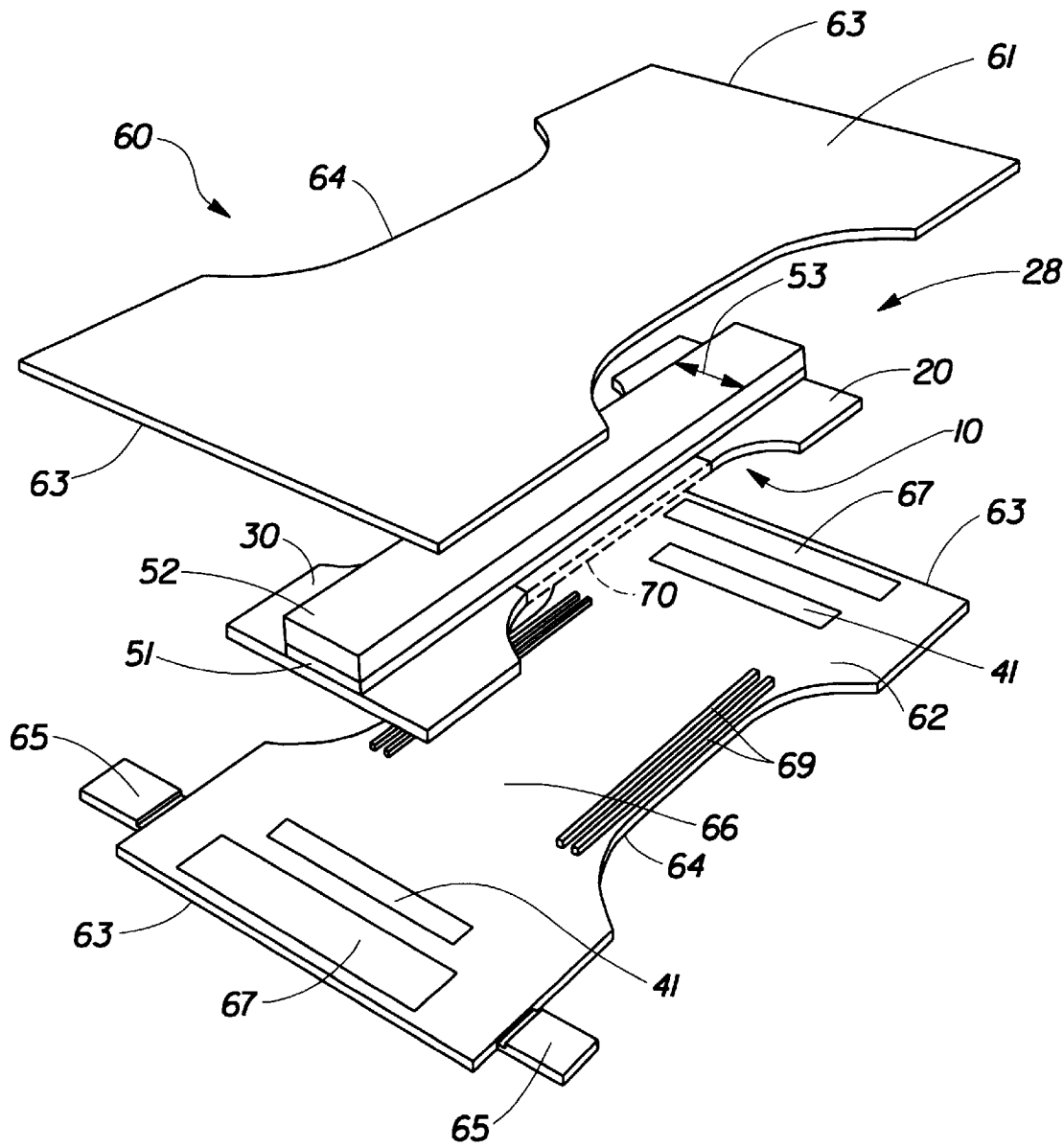
FIG. 1 of the drawings is a blown-apart view of a diaper having an absorbent core which comprises a high capillary suction capacity storage element of the present invention.

I. Characteristics Important to Distributing Aqueous Liquids

The materials of the present invention have a reduced CDH to CAH ratio compared with materials previously used in the liquid absorbency field. (Methods for measuring CDH and CAH are described in detail in Test Methods section below.) Most prior absorbent materials have a ratio of CDH:CAH of at least about 2:1. As discussed above, the increased forces needed to desorb the material, relative to the absorption forces exhibited by the material, is the result of capillary hysteresis. For the materials of the present invention, the CDH:CAH ratio has been significantly reduced, such that the CDH:CAH ratio is not more than about 1.8:1. This surprising reduction in hysteresis provides materials which are particularly suitable as liquid distribution components in absorbent articles. Thus, when employed specifically to provide a distribution function, the materials of the present invention are readily able to dewater liquid acquisition materials and are themselves readily dewatered by higher suction materials such as liquid storage materials. Nonetheless, while the materials of the present invention are referred to herein as "distribution materials", because of their reduced hysteresis character and their ability to transport liquid, the materials may be designed to function as liquid acquisition materials or as liquid storage materials. In this regard, the materials of the present invention may be employed as liquid acquisition materials, liquid distribution materials and/or liquid storage materials in absorbent articles.

The distribution materials of the present invention also have a maximum CDH so that the distribution material can subsequently be dewatered by the storage material, and a minimum wicking rate to ensure that the material wicks liquid away from the acquisition zone of the absorbent core before the next liquid insult occurs. (A method for measuring wicking rate is also described in the Test Methods section.) The materials also preferably have a minimum CAH so the acquisition component of the core can be effectively dewatered by the distribution material.

The distribution material of the present invention should also be efficient with respect to use of material. This requires a minimum absorbent capacity at a given height in the capillary absorption experiment, as described in detail in the Test Methods section .

When the above properties are carefully balanced, the distribution materials have the ability to acquire liquids from an acquisition component, wick those liquids against gravity to higher portions of the absorbent core, and release the aqueous liquids to the storage component.

A. Capillary Desorption Height (CDH)

CDH is determined by draining (via gravity) a sufficiently long strip of the distribution material previously saturated in the aqueous liquid. Capillary desorption pressure refers to the material's ability to hold onto liquid at various hydrostatic heads at equilibrium conditions at 31° C. For the purposes of the present invention, the capillary desorption pressure of interest is the hydrostatic head (i.e., height) at which the liquid loading is 50% of the free absorbent capacity under equilibrium conditions at 31° C.

The capillary desorption pressure is important relative to the absorption pressure of other absorbent components, especially those intended for liquid storage. If the liquid distribution component of the absorbent article holds the acquired liquid too tenaciously, this will inhibit the ability of these other components to partition liquid away. This can cause the distribution component to remain so heavily loaded with liquid that the absorbent article is more susceptible to leaking. For most materials, the CDH is about twice the value of the CAH due to capillary hysteresis. For the distribution materials of the present invention, the CDH value is not more than about 1.8 times the CAH of the material. In particular, the distribution material of the present invention has a CDH value of not more than about 50 cm, preferably not more than about 45 cm, and more preferably not more than about 40 cm. Typically, the distribution material will have a CDH value of from about 12 cm to about 50 cm, more typically from about 15 to about 45 cm, still more typically from about 20 to about 40 cm.

Because of their relatively low CDH values, the distribution materials of the present invention can be readily desorbed by other components of the absorbent core that store such liquids, including those comprising conventional absorbent gelling materials such as are disclosed in, for example, U.S. Pat. No. 5,061,259 (Goldman et al.), issued Oct. 29, 1991, U.S. Pat. No. 4,654,039 (Brandt et al.), issued Mar. 31, 1987 (reissued Apr. 19, 1988 as Re. 32,649), U.S. Pat. No. 4,666,983 (Tsubakimoto et al.), issued May 19, 1987, and U.S. Pat. No. 4,625,001 (Tsubakimoto et al.), issued Nov. 25, 1986, all of which are incorporated by reference; as well as absorbent macrostructures made from these absorbent gelling materials such as those disclosed in, for example, U.S. Pat. No. 5,102,597 (Roe et al.), issued Apr. 7, 1992, and U.S. Pat. No. 5,324,561 (Rezai et al.), issued Jun. 23, 1994, both of which are incorporated by reference). Indeed, these distribution materials can be most readily desorbed by absorbent polymeric foams that store the acquired liquid, such as those disclosed in, for example, U.S. Pat. No. 5,268,224 (DesMarais et al.), issued Dec. 7, 1993; U.S. Pat. No. 5,387,207 supra, U.S. Pat. No. 5,563,179 supra; U.S. Pat. No. 5,560,222 (DesMarais et al.), issued Jul. 22, 1997, and copending U.S. patent application Ser. No. 09/042,429, (pending), filed Mar. 13, 1998 by T. A. DesMarais entitled "HIGH SUCTION POLYMERIC FOAM MATERIALS" (P&G Case 7052); and mixtures of absorbent gelling materials with the aforementioned polymeric foams or other absorbents of very high surface areas such as those described in co-pending U.S. patent application Ser. No. 09/041,930, (pending) filed Mar. 13, 1998 by G. A. Young et al. entitled "ABSORBENT MEMBERS COMPRISING A HIGH SURFACE AREA MATERIAL FOR ABSORBING BODY LIQUIDS" (P&G Case 7053) and U.S. patent application Ser. No. 09/042,435, (pending) filed Mar. 13, 1998 by G. A. Young et al. entitled "ABSORBENT MEMBERS FOR ABSORBING BODY LIQUIDS" (P&G Case 7054); the disclosure of each of which is incorporated by reference. Accordingly, the distribution materials of the present invention function very well in multiple "gush" situations to move the acquired liquid rapidly to other liquid storage components of the absorbent structure.

B. Capillary Absorption Height (CAH)

Another important property of useful distribution materials according to the present invention is their capillary absorption pressure. This technique provides the capacity of the material as a function of varying hydrostatic pressures exerted by the force of gravity on the column of water contained therein. Capillary absorption pressure refers to the ability of the foam to wick liquid vertically. For the purposes of the present invention, the capillary absorption pressure of interest is the hydrostatic head at which the vertically wicked liquid loading is 50% of the free absorbent capacity under equilibrium conditions at 31° C. The hydrostatic head is represented by a column of liquid (e.g., synthetic urine) of height h. [See P. K. Chatterjee and H. V. Nguyen in "Absorbency," Textile Science and Technology, Vol. 7; P. K. Chatterjee, Ed.; Elsevier: Amsterdam, 1985; Chapter 2.]. The CAH value must be at least about that of the height of the absorbent core when the product is worn in an upright position. E.g., a small diaper used for small infants may require a CAH of only about 10–12 cm. A large product intended for use by adults for incontinence may require a 20–25 cm CAH. The absorbent materials of the present invention can be designed so as to have the minimum CAH required for the functioning of the specific product under consideration.

C. Ratio of CDH to CAH

As discussed above, an important aspect of the present distribution materials is their reduced hysterisis, which is reflected in relatively low CDH to CAH ratios. The materials of the present invention have a ratio of CDH:CAH of not more than about 1.8:1, preferably not more than about 1.7:1, more preferably not more than about 1.6:1, still more preferably not more than about 1.5:1, still more preferably not more than about 1.4:1, still more preferably not more than about 1.3:1, still more preferably not more than about 1.2:1, still more preferably not more than about 1.1:1.

D. Wicking Rate

Another important requirement of the distribution material of the present invention is that it be sufficiently hydrophilic and porous so that it wicks liquid rapidly to the height desired for functionality within an absorbent structure. Wicking rate is measured as described in the Test Methods section of U.S. Pat. No. 5,563,179, supra. To be especially useful in absorbent articles for absorbing urine, the distribution material of the present invention will vertically wick synthetic urine (65+5 dynes/cm) to a height of 15 cm in no more than about 25 minutes. More preferably, the distribution material will vertically wick this synthetic urine to a height of 15 cm in no more than about 20 minutes, still more preferably in no more than about 15 minutes, and most preferably in no more than about 10 minutes. Typically, the distribution material will vertically wick synthetic urine to a height of 15 cm in from about 3 to about 25 minutes, more typically from about 3 to about 20 minutes, and more typically from about 4 to about 15 minutes.

E. Vertical Wicking Capacity

The vertical wicking absorbent capacity test measures the amount of test liquid per gram of distribution material that is held within each one inch (2.54 cm) vertical section of the same standard size sample used in the vertical wicking test. Such a determination is generally made after the sample has been allowed to vertically wick test liquid to equilibrium (e.g., after about 18 hours). The vertical wicking absorbent capacity test is described in greater detail in the Test Methods section of U.S. Pat. No. 5,387,207.

The distribution material of the present invention will have a vertical wicking capacity of at least about 6 g/g, preferably at least about 7 g/g, still more preferably at least about 9 g/g, at a height of 15 cm. Preferably, the distribution material will have a vertical wicking capacity at 15 cm of from about 6 g/g to about 120 g/g, more preferably from about 7 g/g to about 85 g/g, still more preferably from about 9 g/g to about 70 g/g.

F. Free Absorbent Capacity

Another relevant property of distribution materials according to the present invention is their free absorbent capacity ("FAC"). "Free absorbent capacity" is the total amount of test liquid (synthetic urine) which a given sample will absorb into its structure per unit mass of solid material in the sample. The distribution materials which are especially useful in absorbent articles such as diapers will at least meet a minimum free absorbent capacity. To be especially useful in absorbent articles for absorbing urine, the distribution materials of the present invention will have a free capacity of at least about 12 g/g, preferably at least about 15 g/g, more preferably at least about 20 g/g, of synthetic urine per gram of dry foam material. Preferably, the free absorbent capacity will be from about 12 to about 125 g/g, more preferably from about 15 to about 90 g/g, and most preferably from about 20 to about 75 g/g, of synthetic urine per gram of dry foam material. The procedure for determining the free absorbent capacity is described in the Test Methods section of U.S. Pat. No. 5,563,179 supra.

II. Preferred Polymeric Distribution Foams

In a preferred embodiment of the present invention, the distribution materials are hydrophilic, flexible polymeric foam structures of interconnected open-cells. The reduced hysteresis of these foam structures is achieved in-part by ensuring that the mechanical strength of the foam is such that, upon giving up its liquid, the foam collapses under the capillary pressures involved. The collapse process reduces the effective foam capacity by a substantial factor related to the density of the foam, as is described hereinafter. The collapse, if relatively uniform throughout the structure, also reduces the amount of liquid held in place at the point of liquid insult. In this regard, the strength of the foams is less than the capillary pressure exerted by the foams such that the foams will collapse when the aqueous liquids are removed by the storage component of the core. Capillary pressure is controlled herein primarily by adjusting foam cell size (which relates inversely to surface area per unit volume). Strength is controlled by the combination of crosslink density and foam density. The type of crosslinker and other comonomers can also be influential.

A. General Distribution Foam Characteristics

Polymeric foams useful herein are those which are relatively open-celled. The cells in such substantially open-celled foam structures have intercellular openings or "windows" that are large enough to permit ready liquid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 1 and 2. For purposes of the present invention, a foam material is "open-celled" if at least 80% of the cells in the foam structure that are at least 1 $\mu$m in size are in fluid communication with at least one adjacent cell.

In addition to being open-celled, these polymeric foams are sufficiently hydrophilic to permit the foam to absorb aqueous liquids. The internal surfaces of the foam structures are rendered hydrophilic by residual hydrophilizing surfactants and/or salts left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the Test Methods section of U.S. Pat. No. 5,387,207 (Dyer et al.) issued Feb. 7, 1995, which is incorporated by reference. Foams which are useful as distribution materials of the present invention are generally those which exhibit an adhesion tension value of from about 15 to about 65 dynes/cm, more preferably from about 20 to about 65 dynes/cm, as determined by capillary suction uptake of synthetic urine having a surface tension of 65±5 dynes/cm.

An important aspect of these foams is their glass transition temperature (Tg). The Tg represents the midpoint of the transition between the glassy and rubbery states of the polymer. Foams that have a higher Tg than the temperature of use can be very strong but can also be very rigid and potentially prone to fracture. Such foams also tend to creep under stress and be poorly resilient when used at temperatures colder than the Tg of the polymer. The desired combination of mechanical properties, specifically strength and resilience, typically necessitates a fairly selective range of monomer types and levels to achieve these desired properties.

For distribution foams of the present invention, the Tg should be as low as possible, so long as the foam has acceptable strength. Accordingly, monomers are selected as much as possible that provide corresponding homopolymers having lower Tg's.

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean transition is incomplete at in-use temperatures. Typically, if the transition is incomplete at the in-use temperature, the polymer will evidence greater rigidity and will be less resilient. Conversely, if the transition is completed at the in-use temperature, then the polymer will exhibit faster recovery from compression. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in U.S. Pat. No. 5,563,179 (Stone et al.) issued Oct. 8, 1996.)

B. Other Properties of Foams Useful Herein

In addition to the requisite properties of CDH, ratio of CDH to CAH, vertical wicking rate, vertical wicking capacity and free absorbent capacity, which is required of any distribution material of the present invention, preferred polymeric foam materials also have other physical properties.

1. Capillary Collapse Pressure (CCP)

Foams of the present invention are able to wick aqueous liquids to a significant height against the force of gravity, e.g., at least about 15 cm. The column of liquid held within the foam exerts a significant contractile capillary pressure. At a height determined by both the strength of the foam (in compression) and the surface area per unit volume of the foam, the foam will collapse. This height, as defined in more detail in the Test Methods section infra, is the Capillary Collapse Pressure (CCP) expressed in cm at which 50% of the volume of the foam at zero head pressure is lost. Preferred distribution foams of the present invention will have a CCP of at least about 15 cm, more preferably at least about 20 cm, still more preferably at least about 25 cm. Typically, preferred distribution foams will have a capillary collapse pressure of from about 15 cm to about 50 cm, more preferably from about 20 cm to about 45 cm, still more preferably from about 25 to about 40 cm.

CCP may also be expressed as yield stress given in units of kPa. Yield stress is determined is a stress-strain experiment in compression mode on absorbent foams. This procedure and intercomversion of yield stress with CCP is given in more detail in the Test Methods section infra.

2. Cell and Hole Sizes

A feature that can be useful in defining preferred polymeric foams is the cell structure. Foam cells, and especially cells that are formed by polymerizing a monomer-containing oil phase that surrounds relatively monomer-free water-phase droplets, will frequently be substantially spherical in shape. These spherical cells are connected to each other by openings, which are referred to hereafter as holes between cells. Both the size or "diameter" of such spherical cells and the diameter of the openings (holes) between the cells are commonly used for characterizing foams in general. Since the cells, and holes between the cells, in a given sample of polymeric foam will not necessarily be of approximately the same size; average cell and hole sizes, i.e., average cell and hole diameters, will often be specified.

Figure 3:
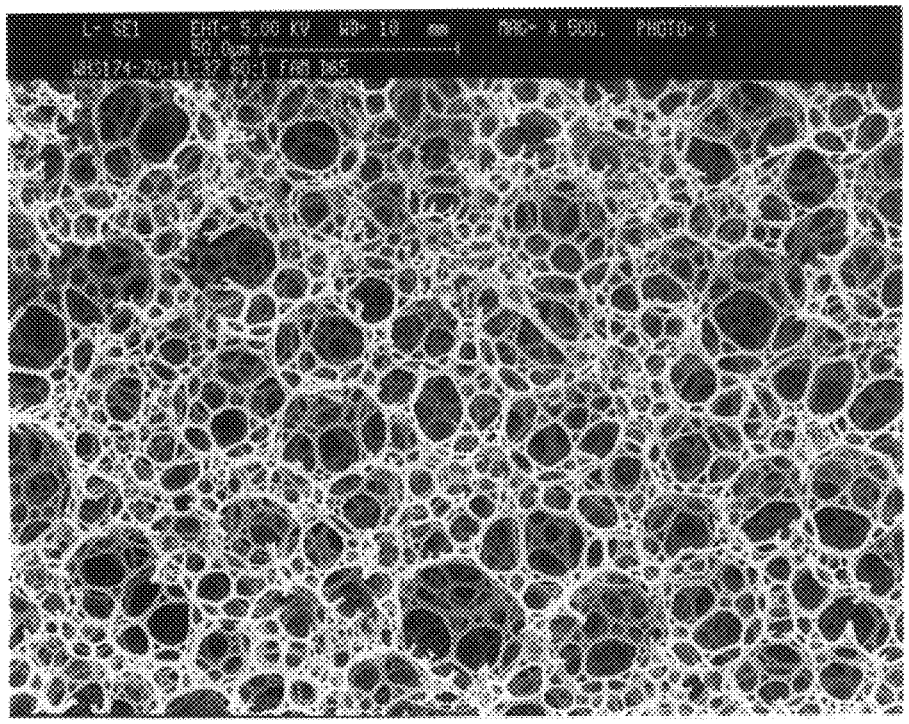
FIG. 3 of the drawings is a photomicrograph (500× magnification) of a section of a representative distribution material according to the present invention made from a HIPE having a 60:1 water-to-oil weight ratio and poured at 77° C., and where the monomer component consisted of a 19:14:55:12 weight ratio of ethyl styrene (EtS):divinyl benzene (DVB):2-ethylhexyl acrylate (EHA):hexanediol diacrylate (HDDA) and where 7.5% (by weight of the oil phase) of diglycerol monooleate (DGMO) and 1% of ditallow dimethyl ammonium methylsulfate emulsifiers were used. The distribution material depicted in FIG. 3 is the polymeric foam material described in Example 2 below.
Figure 4:
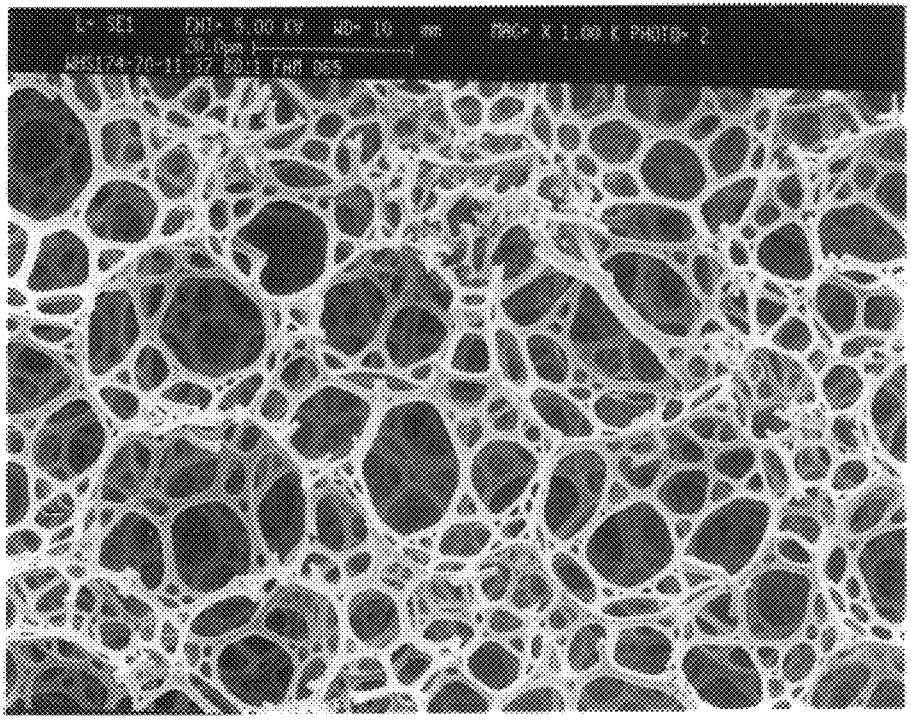
FIG. 4 of the drawings is a photomicrograph (1000× magnification) of the foam of FIG. 3.

Cell and hole sizes are parameters that can impact a number of important mechanical and performance features of the foams according to the present invention, including the liquid wicking properties of these foams, as well as the capillary pressure that is developed within the foam structure. A number of techniques are available for determining the average cell and hole sizes of foams. A useful technique involves a simple measurement based on the scanning electron photomicrograph of a foam sample. FIGS. 3 and 4, for example, show a typical HIPE foam structure according to the present invention. For example, superimposed on the photomicrograph of FIG. 4 is a scale representing a dimension of 20 $\mu$m. Such a scale can be used to determine average cell and hole sizes by an image analysis procedure. The foams useful as absorbents for aqueous liquids in accordance with the present invention will preferably have a number average cell size of from about 20 $\mu$m to about 100 $\mu$m, and typically from about 30 $\mu$m to about 90 $\mu$m, and a number average hole size of from about 5 $\mu$m to about 15 $\mu$m, and typically from about 5 $\mu$m to about 12 $\mu$m.

3. Capillary Suction Specific Surface Area

"Capillary suction specific surface area" is a measure of the test-liquid-accessible surface area of the polymeric network accessible to the test liquid. Capillary suction specific surface area is determined both by the dimensions of the cellular units in the foam and by the density of the polymer, and is thus a way of quantifying the total amount of solid surface provided by the foam network to the extent that such a surface participates in absorbency.

For purposes of this invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the Test Methods section of U.S. Pat. No. 5,387,207 supra. Any reasonable alternative method for determining capillary suction specific surface area can also be utilized.

Distribution foams of the present invention useful will preferably have a capillary suction specific surface area of at least about 0.01 m$^2$/mL, more preferably at least about 0.03 m$^2$/mL. Typically, the capillary suction specific surface area is in the range from about 0.01 to about 0.20 m$^2$/mL, preferably from about 0.03 to about 0.10 m$^2$/mL, most preferably from about 0.04 to about 0.08 m$^2$/mL.

4. Foam Density

"Foam density" (i.e., in grams of foam per cubic centimeter of foam volume in air) is specified herein on a dry basis. The density of the foam, like capillary suction specific surface area, can influence a number of performance and mechanical characteristics of absorbent foams. These include the absorbent capacity for aqueous liquids and the compression deflection characteristics. Foam density will vary according to the state of the foam. Foams in the collapsed state obviously have higher density than the same foam in the fully expanded state. In general, foams in the collapse state of the present invention have a dry density of about 0.11 g/cc. As a nonlimiting example, a foam having an expanded density of about 20 mg/cc will have a Free Absorbent Capacity (FAC) of about 50 g/g. When in the collapsed state, the FAC is reduced commensurate with the reduction in void volume caused by the collapse, which would be a factor of about 5 in this example. Thus, the FAC in the collapsed state will be only about 10–11 g/g. This reversible collapsing process allows for the unusually low CDH:CAH ratios achieved by the foams of the present invention.

Any suitable gravimetric procedure that will provide a determination of mass of solid foam material per unit volume of foam structure can be used to measure foam density. For example, an ASTM gravimetric procedure described more fully in the Test Methods section of U.S. Pat. No. 5,387,207 supra is one method that can be employed for density determination. Foam density pertains to the weight per unit volume of a washed foam free of emulsifiers, fillers, surface treatments such as salts, and the like. The foams of the present invention will preferably have dry densities of from about 8 mg/cc to about 77 mg/cc, more preferably from about 11 mg/cc to about 63 mg/cc, still more preferably from about 13 mg/cc to about 48 mg/cc.

III. Preparation of Polymeric Distribution Foams From HIPEs

The present invention further relates to a process for obtaining the preferred distribution foams by polymerizing a specific type of water-in-oil emulsion or HIPE having a relatively small amount of an oil phase and a relatively greater amount of a water phase. This process comprises the steps of:

A) forming a water-in-oil emulsion at a specified temperature and under specified shear mixing from:
  1) an oil phase comprising:
    a) from about 85 to about 98% by weight of a monomer component capable of forming a copolymer having a Tg of about 35° C. or lower, the monomer component comprising:
      i) from about 30 to about 80% by weight of at least one substantially water-insoluble monofunctional monomer capable of forming an atactic amorphous polymer having a Tg of about 25° C. or lower;
      ii) from about 5 to about 40% by weight of at least one substantially water-insoluble monofunctional comonomer capable of imparting toughness about equivalent to that provided by styrene;
      iii) from about 5 to about 30% by weight of a first substantially water-insoluble, polyfunctional crosslinking agent selected from divinyl benzenes, trivinylbenzenes, divinyltoluenes, divinylxylenes, divinylnaphthalenes divinylalkylbenzenes, divinylphenanthrenes, divinylbiphenyls, divinyldiphenylmethanes, divinylbenzyls, divinylphenylethers, divinyldiphenylsulfides, divinylfurans, divinylsulfide, divinyl sulfone, and mixtures thereof; and
      iv) from about 0 to about 15% by weight of a second substantially water-insoluble, polyfunctional crosslinking agent selected from polyfunctional acrylates, methacrylates, acrylamides, methacryl-amides, and mixtures thereof; and
    b) from about 2 to about 15% by weight of an emulsifier component which is soluble in the oil phase and which is suitable for forming a stable water-in-oil emulsion, the emulsion component comprising:
      (i) a primary emulsifier having at least about 40% by weight emulsifying components selected from diglycerol monoesters of linear unsaturated $C_{16}$–$C_{22}$ fatty acids, diglycerol monoesters of branched $C_{16}$–$C_{24}$ fatty acids, diglycerol monoaliphatic ethers of branched $C_{16}$–$C_{24}$ alcohols, diglycerol monoaliphatic ethers of linear unsaturated $C_{16}$–$C_{22}$ fatty alcohols, diglycerol monoaliphatic ethers of linear saturated $C_{12}$–$C_{14}$ alcohols, sorbitan monoesters of linear unsaturated $C_{16}$–$C_{22}$ fatty acids, sorbitan monoesters of branched $C_{16}$–$C_{24}$ fatty acids, and mixtures thereof; or
      (ii) the combination a primary emulsifier having at least 20% by weight of these emulsifying components and certain secondary emulsifiers in a weight ratio of primary to secondary emulsifier of from about 50:1 to about 1:4; and
  2) a water phase comprising an aqueous solution containing: (i) from about 0.2 to about 20% by weight of a water-soluble electrolyte; and (ii) an effective amount of a polymerization initiator;
  3) a volume to weight ratio of water phase to oil phase in the range of from about 12:1 to about 125:1; and
B) polymerizing the monomer component in the oil phase of the water-in-oil emulsion to form a polymeric foam material; and
C) optionally dewatering the polymeric foam material.

The process of the present invention allows the formation of these absorbent foams that are capable of distributing liquids as a result of having carefully balanced properties as described above. These properties are achieved by careful selection of crosslinker and monomer types and levels and emulsion formation parameters, specifically the amount of shear mixing, the temperature, and the water-to-oil ratio (which translates into the final density of the dry foam).

A. In General

Polymeric foams according to the present invention can be prepared by polymerization of certain water-in-oil emulsions having a relatively high ratio of water phase to oil phase commonly known in the art as "HIPEs. Polymeric foam materials which result from the polymerization of such emulsions are referred to hereafter as "HIPE foams." A detailed description of the general preparation of such HIPEs is given in U.S. Pat. No. 5,563,179 and U.S. Pat. No. 5,387,207, infra.

The relative amounts of the water and oil phases used to form the HIPEs are, among many other parameters, important in determining the structural, mechanical and performance properties of the resulting polymeric foams. In particular, the ratio of water to oil ("W:O ratio") in the emulsion varies inversely with ultimate foam density and can influence the cell size and capillary suction specific surface area of the foam and dimensions of the struts that form the foam. The emulsions used to prepare the HIPE foams of this invention will generally have a volume to weight ratio of water phase to oil phase in the range of from about 12:1 to about 125:1, and most typically from about 15:1 to about 90:1. Particularly preferred foams can be made from HIPEs having ratios of from about 20:1 to about 75:1.

1. Oil Phase Components

The major portion of the oil phase of the HIPEs will comprise monomers, comonomers and crosslinking agents such as those enumerated in U.S. Pat. No. 5,387,207 infra. It is essential that these monomers, comonomers and crosslinking agents be substantially water-insoluble so that they are primarily soluble in the oil phase and not the water phase. Use of such substantially water-insoluble monomers ensures that HIPEs of appropriate characteristics and stability will be realized. It is, of course, highly preferred that the monomers, comonomers and crosslinking agents used herein be of the type such that the resulting polymeric foam is suitably non-toxic and appropriately chemically stable. These monomers, comonomers and cross-linking agents should preferably have little or no toxicity if present at very low residual concentrations during post-polymerization foam processing and/or use.

Another essential component of the oil phase is an emulsifier component that permits the formation of stable HIPEs. This emulsifier component comprises a primary emulsifier and optionally a secondary emulsifier, such as those enumerated in U.S. Pat. No. 5,387,207 infra.

The oil phase used to form the HIPEs comprises from about 85 to about 98% by weight monomer component and from about 2 to about 15% by weight emulsifier component. Preferably, the oil phase will comprise from about 90 to about 98% by weight monomer component and from about 3 to about 10% by weight emulsifier component. The oil phase also can contain other optional components. One such optional component is an oil soluble polymerization initiator of the general type well known to those skilled in the art, such as described in U.S. Pat. No. 5,290,820 (Bass et al.), issued Mar. 1, 1994, which is incorporated by reference. Another preferred optional component is an antioxidant such as a Hindered Amine Light Stabilizer (HALS) and Hindered Phenolic Stabilizers (HPS) or any other antioxidant compatible with the initiator system to be employed. Other optional components include plasticizers, fillers, colorants, chain transfer agents, dissolved polymers, and the like.

2. Water Phase Components

The discontinuous water internal phase of the HIPE is generally an aqueous solution containing one or more dissolved components such as those enumerated in U.S. Pat. No. 5,387,207 infra. One essential dissolved component of the water phase is a water-soluble electrolyte. The dissolved electrolyte minimizes the tendency of the monomers, comonomers and crosslinkers that are primarily oil soluble to also dissolve in the water phase. This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

The HIPEs will also typically contain a polymerization initiator. Such an initiator component is generally added to the water phase of the HIPEs and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase.

3. Hydrophilizing Surfactants and Hydratable Salts

The polymer forming the HIPE foam structure will preferably be substantially free of polar functional groups. This means the polymeric foam will be relatively hydrophobic in character. These hydrophobic foams can find utility where the absorption of hydrophobic liquids is desired. Uses of this sort include those where an oily component is mixed with water and it is desired to separate and isolate the oily component, such as in the case of marine oil spills.

When these foams are to be used as absorbents for aqueous liquids such as juice spills, milk, and the like for clean up and/or bodily liquids such as urine, they generally require further treatment to render the foam relatively more hydrophilic. Hydrophilization of the foam, if necessary, can generally be accomplished by treating the HIPE foam with a hydrophilizing surfactant in a manner described in U.S. Pat. No. 5,387,207 infra.

These hydrophilizing surfactants can be any material that enhances the water wettability of the polymeric foam surface. They are well known in the art, and can include a variety of surfactants, preferably of the nonionic type, such as those enumerated in U.S. Pat. No. 5,387,207 infra.

Another material that is typically incorporated into the HIPE foam structure is a hydratable, and preferably hygroscopic or deliquescent, water soluble inorganic salt. Such salts include, for example, toxicologically acceptable alkaline earth metal salts. Salts of this type and their use with oil-soluble surfactants as the foam hydrophilizing surfactant is described in greater detail in U.S. Pat. No. 5,352,711 (DesMarais), issued Oct. 4, 1994, the disclosure of which is incorporated by reference. Preferred salts of this type include the calcium halides such as calcium chloride that, as previously noted, can also be employed as the water phase electrolyte in the HIPE.

Hydratable inorganic salts can easily be incorporated by treating the foams with aqueous solutions of such salts. These salt solutions can generally be used to treat the foams after completion of, or as part of, the process of removing the residual water phase from the just-polymerized foams. Treatment of foams with such solutions preferably deposits hydratable inorganic salts such as calcium chloride in residual amounts of at least about 0.1% by weight of the foam, and typically in the range of from about 0.1 to about 12%.

Treatment of these relatively hydrophobic foams with hydrophilizing surfactants (with or without hydratable salts)

will typically be carried out to the extent necessary to impart suitable hydrophilicity to the foam. Some foams of the preferred HIPE type, however, are suitably hydrophilic as prepared, and can have incorporated therein sufficient amounts of hydratable salts, thus requiring no additional treatment with hydrophilizing surfactants or hydratable salts. In particular, such preferred HIPE foams include those where certain oil phase emulsifiers previously described and calcium chloride are used in the HIPE. In those instances, the internal polymerized foam surfaces will be suitably hydrophilic, and will include residual water-phase liquid containing or depositing sufficient amounts of calcium chloride, even after the polymeric foams have been dewatered to a practicable extent.

B. Processing Conditions for Obtaining HIPE Foams

Foam preparation typically involves the steps of: 1) forming a stable high internal phase emulsion (HIPE); 2) polymerizing/curing this stable emulsion under conditions suitable for forming a solid polymeric foam structure; 3) optionally washing the solid polymeric foam structure to remove the original residual water phase from the polymeric foam structure and, if necessary, treating the polymeric foam structure with a hydrophilizing surfactant and/or hydratable salt to deposit any needed hydrophilizing surfactant/ hydratable salt, and 4) thereafter dewatering this polymeric foam structure. The procedure is described more fully in U.S. Pat. No. 5,387,207 supra.

IV. Uses of Distribution Materials of the Present Invention

A. In General

Distribution materials according to the present invention are broadly useful in absorbent cores of disposable diapers, as well as other absorbent articles. These materials can also be employed in other absorbent articles, especially when there is a need to wick liquid to some height against the force of gravity and then release the liquid to another storage element within the product.

B. Absorbent Articles

The liquid distribution materials of the present invention are particularly useful in absorbent structures (e.g., absorbent cores or core elements) for various absorbent articles. By "absorbent article" herein is meant a consumer product that is capable of absorbing significant quantities of urine, menses, or other liquids (i.e., liquids), such as aqueous fecal matter (runny bowel movements), discharged by an incontinent wearer or user of the article. Examples of such absorbent articles include disposable diapers, incontinence garments, catamenials such as tampons and sanitary napkins, disposable training pants, bed pads, and the like. The distribution materials described herein are particularly suitable for use in articles such as diapers, incontinence pads or garments, clothing shields, and the like.

In its simplest form, where the distribution material exhibits sufficient liquid storage capacity, an absorbent article of the present invention need only include a backing sheet, typically relatively liquid-impervious, an acquisition material, and the distribution material. The components will be associated such that the acquisition material is closest to the liquid discharge region or insult zone of the wearer of the absorbent article. Next is the liquid distribution/storage member backed by the backing sheet. Liquid impervious backing sheets can comprise any material, for example polyethylene or polypropylene, having a thickness of about 1.5 mils (0.038 mm), which will help retain liquid within the absorbent article.

More conventionally, these absorbent articles will also include a liquid-pervious topsheet element that covers the side of the absorbent article that touches the skin of the wearer. In this configuration, the article includes an absorbent core comprising one or more liquid distribution materials of the present invention positioned between the backing sheet and the topsheet. In particularly preferred embodiment, the article's absorbent core will comprise a separate liquid storage layer. Liquid-pervious topsheets can comprise any material such as polyester, polyolefin, rayon and the like that is substantially porous and permits body liquid to readily pass there through and into the underlying absorbent core. The topsheet material will preferably have no propensity for holding aqueous liquids in the area of contact between the topsheet and the wearer's skin.

As indicated, in addition to the distribution member of the present invention, the absorbent core of the absorbent articles herein can also comprise other, e.g., conventional, elements or materials. In one embodiment involving a combination of the distribution member herein and other absorbent materials, the absorbent articles can employ a multi-layer absorbent core configuration where a core layer containing one or more distribution materials of the present invention can be used in combination with one or more additional separate core layers comprising other absorbent structures or materials. These other absorbent structures or materials, for example, can include air-laid or wet-laid webs of wood pulp or other cellulosic fibers. These other absorbent structures can also comprise foams, e.g., absorbent foams or even sponges useful as liquid acquisition/ distribution components such as those disclosed in U.S. Pat. No. 5,563,179 (Stone et al.), supra.

A preferred embodiment entails a further separation of the various absorbent core elements. This preferred absorbent core comprises an acquisition layer only around the crotch region of the wearer to manage the initial rapid liquid gush. The distribution layer (comprising a material of the present invention) is positioned vertically to the front and back of the acquisition layer so as to wick the liquid out of the crotch region, not just from the front to the back. A distinct storage layer is positioned in a position above the acquisition layer (with an assumed standing position of the wearer) and is in contact only with the distribution material. The storage absorbent member(s) then must be able to absorb the liquid from the distribution layer, overcoming both the force due to gravity and that due to the desorption pressures of the distribution material. The product so depicted removes liquid from the crotch region within the time provided between insults, leaving the acquisition region relatively dry and ready for further uptake of liquid. This further maintains the shape of the garment and keeps the crotch area relatively dry for better skin health.

FIG. 1 shows a preferred embodiment of a diaper 60 in which the topsheet 61 and the backsheet 62 are co-extensive and have length and width dimensions generally larger than those of the absorbent core 28. The topsheet 61 is joined with and superimposed on the backsheet 62 thereby forming the periphery of the diaper 60. The periphery defines the outer perimeter or the edges of the diaper 60.

The topsheet 61 is compliant, soft feeling, and non-irritating to the wearer's skin. Further, the topsheet 61 is liquid pervious permitting liquids to readily penetrate through its thickness. A suitable topsheet 61 can be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. In one embodiment, the topsheet 61 is made of a hydrophobic material to isolate the wearer's skin from liquids in the absorbent core 10. Preferably the topsheet comprises a means to adjust hydrophilicity of the material. In the case of nonwoven topsheets, this can be done by adjusting the surface energy of the fibers before the non-woven is formed, or by adjusting the surface energy of the non-woven after it is formed. The hydrophilicity adjustments can be made such it washes away easily upon wetting such as with urine, or, preferably, such that it remains effective even upon repeated wettings, though possibly at reduced level. Such hyrophilicity adjustments can be incorporated into the resin of the fibers, or can be applied to the fibers just after they are spun, or after the web is formed. In the case of formed and/or apertured films, the surface energy adjustments can be applied to the resin that is formed into the film, or to the surface of the film after formation. Alternatively, combination composites of both nonwovens and films may be used, and for the hydrophilicity adjustment the respective options of both can be applied. A particularly preferred topsheet 61 comprises staple length polypropylene fibers having a denier of about 1.5, such as Hercules type 151 polypropylene marketed by Hercules, Inc. of Wilmington, Del. As used herein, the term "staple length fibers" refers to those fibers having a length of at least about 15.9 mm (0.62 inches).

There are a number of manufacturing techniques which can be used to manufacture the topsheet 61. For example, the topsheet 61 can be woven, nonwoven, spunbonded, carded, or the like. A preferred topsheet is carded, and thermally bonded by means well known to those skilled in the fabrics art. Preferably, the topsheet 61 has a weight from about 18 to about 25 grams per square meter, a minimum dry tensile strength of at least about 400 grams per centimeter in the machine direction, and a wet tensile strength of at least about 55 grams per centimeter in the cross-machine direction.

While it is preferred to have a topsheet as the material nearest the wearer's skin, it is not necessary. It is contemplated that a suitable absorbent core configuration could be used without a topsheet and still produce desirable results such as comfort and absorbency as well as simplicity in manufacturing and material cost savings. For example, the body-side surface of the absorbent core itself could be made of liquid pervious, soft, compliant, non-irritating materials that substitute for a separate topsheet. Such an absorbent core would only need to be used in combination with a backsheet to provide for comfort and absorbency in an absorbent article.

The backsheet 62 is impervious to liquids and is preferably manufactured from a thin plastic film, although other flexible liquid impervious materials may also be used. The backsheet 62 prevents the exudates absorbed and contained in the absorbent core 10 from wetting articles which contact the diaper 60 such as bed sheets and undergarments. Preferably, the backsheet 62 is polyethylene film having a thickness from about 0.012 mm (0.5 mil) to about 0.051 centimeters (2.0 mils), although other flexible, liquid impervious materials can be used. As used herein, the term "flexible" refers to materials which are compliant and which will readily conform to the general shape and contours of the wearer's body.

A suitable polyethylene film is manufactured by Monsanto Chemical Corporation and marketed in the trade as Film No. 8020. The backsheet 62 is preferably embossed and/or matte finished to provide a more clothlike appearance. Further, the backsheet 62 may be "breathable," permitting vapors to escape from the absorbent core 28 while still preventing exudates from passing through the backsheet 62. It is contemplated that a backsheet that is highly breathable but substantially impervious to liquid may be desirable for certain absorbent articles.

The size of the backsheet 62 is dictated by the size of the absorbent core 28 and the exact diaper design selected. In a preferred embodiment, the backsheet 62 has a modified hourglass-shape extending beyond the absorbent core 28 a minimum distance of at least about 1.3 centimeters to at least about 2.5 centimeters (about 0.5 to about 1.0 inch) around the entire diaper periphery.

The topsheet 61 and the backsheet 62 are joined together in any suitable manner. As used herein, the term "joined" encompasses configurations whereby the topsheet 61 is directly joined to the backsheet 62 by affixing the topsheet 61 directly to the backsheet 62, and configurations whereby the topsheet 61 is indirectly joined to the backsheet 62 by affixing the topsheet 61 to intermediate members which in turn are affixed to the backsheet 62. In a preferred embodiment, the topsheet 61 and the backsheet 62 are affixed directly to each other in the diaper periphery by attachment means (not shown) such as an adhesive or any other attachment means as known in the art. For example, a uniform continuous layer of adhesive, a patterned layer of adhesive, or an array of separate lines or spots of adhesive can be used to affix the topsheet 61 to the backsheet 62.

Tape tab fasteners 65 are typically applied to the waistband region 63 of the diaper 60 to provide a fastening means for holding the diaper on the wearer. The tape tab fasteners 65 depicted are representative only. The tape tab fasteners can be any of those well known in the art, such as the fastening tape disclosed in U.S. Pat. 3,848,594 (Buell), issued Nov. 19, 1974, which is incorporated by reference. These tape tab fasteners or other diaper fastening means are typically applied near the corners of the diaper 60.

Elastic members 69 are disposed adjacent the periphery of the diaper 60, preferably along each longitudinal egde 64, so that the elastic members tend to draw and hold the diaper 60 against the legs of the wearer. Additionally, elastic members 67 can be disposed adjacent either or both of the waistband regions 63 of the diaper 60 to provide a waistband as well as or rather than leg cuffs. For example, a suitable waistband is disclosed in U.S. Pat. No. 4,515,595 (Kievit et al.), issued May 7, 1985, which is incorporated by reference. In addition, a method and apparatus suitable for manufacturing a disposable diaper having elastically contractible elastic members is described in U.S. Pat. No. 4,081,301 (Buell), issued Mar. 28, 1978, which is incorporated by reference.

The elastic members are secured to the diaper 60 in an elastically contractible condition so that in a normally unrestrained configuration, the elastic members effectively contract or gather the diaper 60. The elastic members can be secured in an elastically contractible condition in at least two ways. For example, the elastic members can be stretched and secured while the diaper 60 is in an uncontracted condition. Alternatively, the diaper 60 can be contracted, for example, by pleating, and the elastic members secured and connected to the diaper 60 while the elastic members are in their unrelaxed or unstretched condition. The elastic members may extend along a portion of the length of the diaper 60. Alternatively, the elastic members can extend the entire length of the diaper 60, or any other length suitable to provide an elastically contractible line. The length of the elastic members is dictated by the diaper design.

In use, the diaper 60 is applied to a wearer by positioning one waistband region under the wearer's back, and drawing the remainder of the diaper 60 between the wearer's legs so that the other waistband region is positioned across the front of the wearer. The tape-tab 65 or other fasteners are then secured preferably to outwardly facing areas of the diaper 60. In use, disposable diapers or other absorbent articles incorporating the liquid absorbent members of the present invention tend to more quickly and efficiently distribute and store liquids and to remain dry due to the high absorbent capacity of the liquid absorbent members. Disposable diapers incorporating the liquid absorbent members of the present invention can also be thinner and more flexible.

When used as an absorbent core in a disposable diaper 60, a preferred embodiment of the core 28 according to the present invention is positioned such that an acquisition strip 52 is in liquid communication with topsheet 61, and serves to quickly acquire and partition body exudates from the wearer's body to an absorptive distribution strip 51. Adhesive bonding of acquisition strip 52 to topsheet 61 may enhance the liquid communication by providing interfacial bonding and preventing topsheet separation from impeding liquid flow. A distribution material 51 of the present invention moves liquid in the x and y dimensions of the core 28 and is subsequently desorbed by the liquid storage component, shown generally as 10. While components 52 and 51 are shown generally as being rectilinear and of equal size, other shapes and size relationships may be utilized. As shown, the generally rectilinear components have a width 53 corresponding to a suitable width for the crotch area 66 of a disposable diaper. As well, the length of the respective core components may be varied to provide a suitable fit for various wearer sizes.

As is shown in FIG. 1, storage component 10 can comprise two separate storage components 20 and 30 such that there is no absorbent storage member element located in the liquid discharge region of the diaper. Because such an absorbent core 10 has little or no liquid storage material (it should be recognized that the distribution material 51 may have significant storage capacity and will contain liquid, at least until it is desorbed by a higher suction storage material) in the center of the core (corresponding to the crotch or liquid discharge region of the core), articles containing such cores may provide improved fit and wearer comfort both when the article is dry and after it has received several loadings of body liquid. See, e.g., co-pending U.S. patent application Ser. No. 08/825,072, (pending) filed Mar. 27, 1997 by G. Young et al., co-pending U.S. patent application Ser. No. 08/825,071, (pending) filed Mar. 27, 1997 by G. LaVon et al., and co-pending U.S. patent application Ser. No. 08/826,208, filed Mar. 27, 1997 by G. Young et al., which issued Oct. 27, 1998 as U.S. Pat. No. 5,827,253.

Figure 2A:
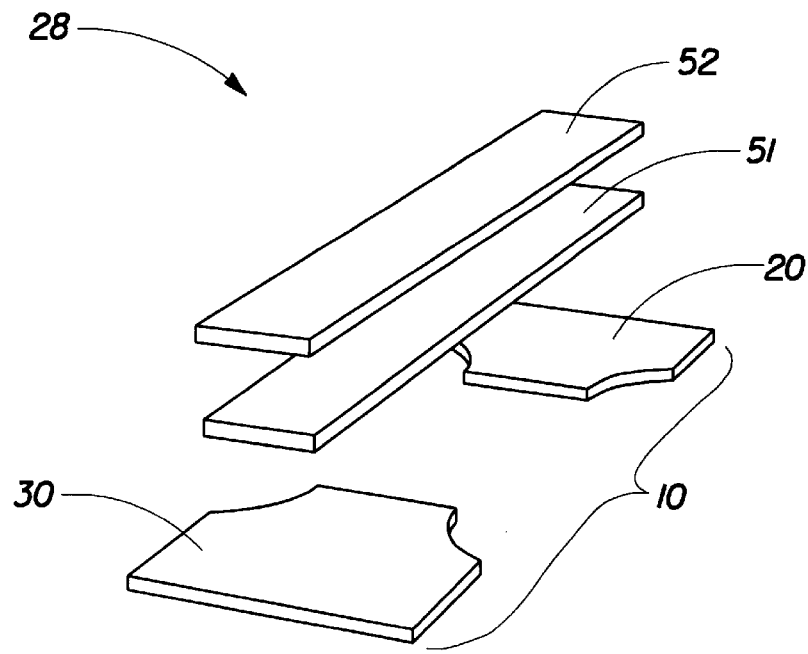
FIG. 2a of the drawings is a blown-apart view of a representative multi-layer core for inclusion in a diaper such as that shown in FIG. 1.

FIG. 2a depicts a blown-apart view of absorbent core 28 having two separated elements 20 and 30, each of which consists of a storage absorbent member that will desorb distribution material 51. Front panel 20 generally corresponds to the portion of the disposable diaper worn in the front of the wearer. Similarly, the back panel 30 corresponds to the portion of the disposable diaper worn in the back of the wearer. In an alternative design where the absorbent core comprises separate liquid storage elements (similar to elements 20 and 30 in FIG. 1 and FIG. 2a), the distribution layer may be positioned below both the acquisition layer(s) and the storage elements. That is, referring to FIG. 1, distribution material 51 would be located below acquisition material 52 and storage elements 20 and 30.

Figure 2B:
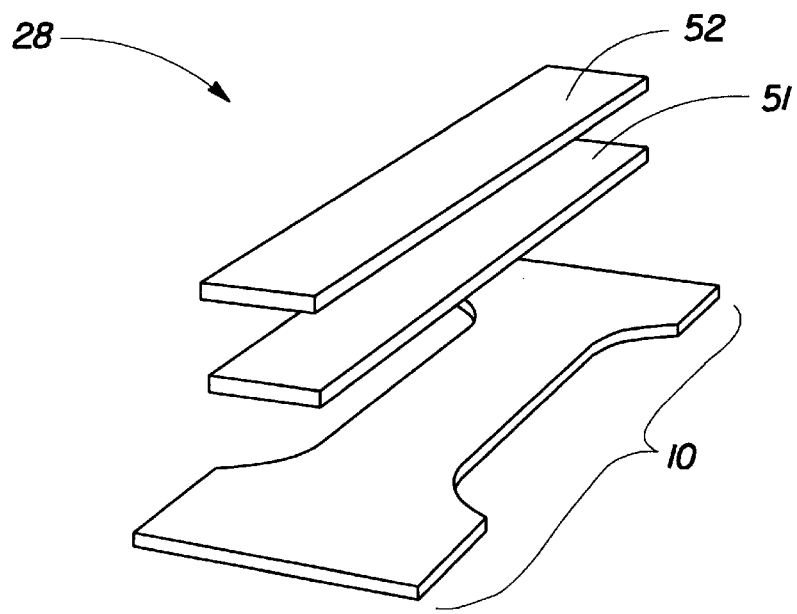
FIG. 2b of the drawings is a blown-apart view of another representative multi-layer core for inclusion in a diaper shown such as that shown in FIG. 1.

Alternatively, storage element 10 may be a unitary layer(s) (i.e., where the dashed lines 70 in FIG. 1 indicate that storage component 10 is included in the liquid discharge region of the article) of storage material. Such an embodiment of an absorbent core 28 is depicted in FIG. 2b.

In one embodiment, aquisition strip 52 will be a liquid handling layer, positioned in the liquid discharge region of the wearer of the article, in the form of a high loft nonwoven, but is preferably in the form of a liquid acquisition comprising a layer of modified cellulosic fibers, e.g., stiffened curled cellulosic fibers, and optionally up to about 10% by weight of this liquid acquisition/distribution layer of polymeric gelling agent. The modified cellulosic fibers used in the liquid acquisition layer 52 of such a preferred absorbent article are preferably wood pulp fibers that have been stiffened and curled by means of chemical and/or thermal treatment. Such modified cellulosic fibers are of the same type as are employed in the absorbent articles described in U.S. Pat. No. 4,935,622 (Lash et al), issued Jun. 19, 1990, which is incorporated by reference. A preferred embodiment is one where the liquid storage layer 10 is as described co-pending U.S. patent application Ser. No. 09/042,429, (pending), filed Mar. 13, 1998 by T. A. DesMarais entitled "HIGH SUCTION POLYMERIC FOAM MATERIALS" (P&G Case 7052); co-pending U.S. patent application Ser. No. 09/041,930, (pending), filed Mar. 13, 1998 by G. A. Young et al. entitled "ABSORBENT MEMBERS COMPRISING A HIGH SURFACE AREA MATERIAL FOR ABSORBING BODY LIQUIDS" (P&G Case 7053); and co-pending U.S. patent application Ser. No. 09/042,435, (pending), filed Mar. 13, 1998 by G. A. Young et al. entitled "ABSORBENT MEMBERS FOR ABSORBING BODY LIQUIDS" (P&G Case 7054). This liquid distribution layer is typically positioned between the (upper) liquid-handling and (lower) higher suction storage layer and is in liquid communication therewith.

As referred to herein, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted). As used herein, the term "diaper" refers to a garment generally worn by infants and incontinent persons that is worn about the lower torso of the wearer. It should be understood, however, that the present invention is also applicable to other absorbent articles such as incontinent briefs, incontinent pads, training pants, diaper inserts, catamenial pads, sanitary napkins, tampons, bandages, facial tissues, paper towels, and the like.

In addition to beneficial liquid handling properties, the preferred absorbent foam materials of the present invention provide good aesthetics due to their soft, resilient structure and physical integrity. In sheet form, these absorbent foams can also be relatively easy to configure for use in a variety of absorbent articles. In contrast to fibrous absorbent components, these absorbent foams remain largely unchanged in overall appearance and structure during use, i.e. density, shape, etc. The thickness of these foams will vary according to the aqueous liquid present in the foam. That is, the foams will be relatively thicker when saturated and relatively collapsed or thinner when dewatered by the contiguous storage layer. Since these absorbent foams are not plasticized by aqueous liquids, their mechanical properties remain largely unchanged when wet.

Because the distribution materials of the present invention efficiently distribute aqueous liquids, they are particularly useful as the liquid distribution component of an absorbent core that benefits from liquid movement. These distribution materials combine relatively high capillary absorption pressures and capacity-per-weight properties that allows them to acquire liquid with or without the aid of gravity, therefore keeping the wearer's skin dry. This high capacity (per given weight) can lead to light-weight, efficient products. In addition, because the distribution materials of the present invention can give up this acquired liquid efficiently to other absorbent components, these materials are particularly useful as a distribution component in a "multi-layer" absorbent core that additionally contains a liquid storage component(s) and a liquid acquisition component.

In some embodiments according to the present invention, the distribution layer of the absorbent core will be placed in a specific positional relationship with respect to the topsheet and the storage layer of the absorbent core. More particularly, the distribution layer of the core is positioned so that it is effectively located to acquire discharged body liquid from the acquisition layer and transport such liquid to other regions of the core. Thus the distribution layer can span between the acquisition zone and some distal storage zone. The acquisition layer would include the crotch area and, preferably for articles to be worn by males, also the region where urination discharges occur in the front of the diaper. For a diaper, the front of the absorbent articles means the portion of the absorbent article which is intended to be placed on the front of the wearer. Additionally, for male wearers, it is desirable for the distribution layer to extend to near the front waist area of the wearer to effectively acquire the relatively high liquid load that occurs in the front of diapers for male wearers, and to compensate for directional variations of the discharges. The corresponding absorbent article regions can vary depending upon the design and fit of the absorbent article.

For diaper executions, the distribution layer of the core can be positioned relative to an elongated topsheet and/or the storage layer such that the distribution layer is of sufficient length to extend to areas corresponding at least to about 50%, preferably at least about 75%, of the length of the topsheet and/or from about 50 to about 200% of the total length of the storage layer(s). The distribution layer should have a width sufficient to acquire body liquids from the acquisition layer. Generally, for diapers, the width of the distribution layer will be at least about 5 cm, preferably at least about 6 cm.

For purposes of determining such distribution layer positioning, the length of the absorbent article will be taken as the normal longest longitudinal dimension of the elongated article backing sheet. This normal longest dimension of the elongated backing sheet can be defined with respect to the article as it is applied to the wearer. When worn, the opposing ends of the back sheet are fastened together so that these joined ends form a circle around the wearer's waist. The normal length of the backing sheet will thus be the length of the line running through the back sheet from a) the point on the edge of the back sheet at the middle of the wearer's back waist, through the crotch, to b) the point on the opposite edge of the backing sheet at the middle of the wearer's front waist. The size and shape of the topsheet will generally correspond substantially to the back sheet.

In the usual instance, the storage layer of the absorbent cores which generally defines the shape of the absorbent article and the normal length of the elongated article topsheet will be approached by the longest longitudinal dimension of the storage layer of the core. However, in some articles (e.g., adult incontinence articles) where bulk reduction or minimum cost are important, the storage layer would be generally located to cover only the genital region of the wearer and a reasonable area proximate to the genital area. In this instance both the liquid distribution layer and the storage layer would be located toward the front of the article as defined by the topsheet such that the distribution and storage layers would typically be found in the front two-thirds of the article length.

The distribution foam layer can be of any desired shape consistent with comfortable fit and the sizing limitations discussed above. These shapes include, for example, circular, rectangular, trapezoidal or oblong, e.g., hourglass-shaped, dog-bone-shaped, half dog bone shaped, oval or irregularly shaped. The distribution foam layer can be of similar shape or differing shape than the storage layer. The storage layer of the preferred absorbent core configuration can also be of any desired shape consistent with comfortable fit including, for example, circular, rectangular, trapezoidal or oblong, e.g., hourglass-shaped, dog-bone-shaped, half dog bone shaped, oval or irregularly shaped. (The storage layer need not be physically separated from the distribution layer or completely unattached from the distribution layer.)

Multi-layer absorbent cores can also be made according to copending U.S. application Ser. No. 08/521,556, filed Aug. 30, 1995 by G. D. LaVon, et al., which was abandoned in favor of continuation application Ser. No. 08/883,810, filed Jun. 27, 1997, which issued Oct. 6, 1998 as U.S. Pat. No. 5,817,081 (herein incorporated by reference), where one or more layers comprise a distribution material of the present invention.

V. Test Methods

The following is a detailed description of the various methods used to characterize the distribution materials of the present invention. It will be recognized that with respect to test methods A, B, C and D, where the test material lacks sufficient integrity to withstand the testing protocol, a hydrophobic screen that does not impact wicking performance can be used to support the material.

A. Vertical Wicking Time and Vertical Wicking Capacity

Vertical wicking time is determined by measuring the time taken for a colored test liquid (e.g., synthetic urine) in a reservoir to wick a vertical distance of 15 cm through a test strip of foam of specified size. The vertical wicking procedure is detailed in the Test Methods section of U.S. Pat. No. 5,387,207 (which is incorporated by reference,) supra, but is performed at 31° C. instead of 37° C. A material's vertical wicking capacity for a given height is measured using the Vertical Wicking Absorbent Capacity Test also described in the Test Methods section of U.S. Pat. No. 5,387,207, except the test is performed at 31° C. instead of 37° C. Finally, the washing and redrying step in the referenced patent is not performed. The vertical wicking capacity value of note is taken as the capacity achieved at a height of 15 cm at equilibrium.

B. Capillary Absorption Pressure

A capillary absorption isotherm curve is generated using the Vertical Wicking Absorbent Capacity test described in the Test Methods section of U.S. Pat. No. 5,387,207 (Dyer et al.), issued Feb. 7, 1995, which is incorporated by reference, except having the test fluid maintained at 31° C. rather than 37° C. The curve is a plot of the absorbent capacity of each segment as a function of wicked height, using the distance from the top of the water reservoir to the midpoint of each segment for the height h. The capillary absorption pressure is taken as the height of the material that has an absorbent capacity one-half of the material's free absorbent capacity (i.e., capacity at a height of 0 cm).

C. Capillary Desorption Pressure

Capillary desorption pressure is a measure of a material's ability to hold onto liquid as a function of various hydrostatic heads. The sample strip of suitable dimensions, e.g., 40 cm long×2.5 cm wide×0.2 cm thick, and the test liquid (distilled water, optionally containing a small amount of food coloring as indicator), are equilibrated in a room at 22±2° C. The measurement is carried out at this same temperature.

The test strip is saturated in water, then positioned vertically such that the lower end is immersed 1–2 mm in a reservoir of water. The water is allowed to drain from the sample until equilibrium is reached, typically 16–24 hours. During this procedure, the sample and reservoir should be shielded, for example by using a glass cylinder and aluminum foil, to prevent water loss due to evaporation. The sample is then quickly removed and placed on a non-absorbent surface where it is cut into 2.5 cm segments after discarding the portion of the sample that was immersed in the reservoir. Each piece is weighed, washed with water, dried and then reweighed. The absorbent capacity is calculated for each piece.

A capillary desorption isotherm curve is generated by plotting the absorbent capacity of each segment as a function of height. The curve is a plot of the absorbent capacity of each segment as a function of height that the test liquid desorbed, using the distance from the top of the water reservoir to the midpoint of each segment for the height h. The capillary desorption pressure is taken as the height of the material that has an absorbent capacity one-half of the foam's free absorbent capacity.

D. Free Absorbent Capacity (FAC)

Free absorbent capacity can be quantified by measuring the amount synthetic urine absorbed in a test sample which has been saturated with synthetic urine. The foam samples and Jayco synthetic urine are equilibrated to a temperature of 31° C. Measurements are performed at ambient temperature.

A test sample sheet is saturated to its free absorbent capacity by soaking in a bath of Jayco synthetic urine. After 3 minutes, a cylinder having a 1 in$^2$ (6.5 cm$^2$) circular surface area is cut out of the saturated, expanded sheet with a sharp circular die. The cylindrical sample is soaked in synthetic urine at 31° C. for a further 3 minutes. The sample is then removed from the synthetic urine and is placed on a digital balance. Any balance fitted with a weighing pan having an area larger than that of the sample and with a resolution of 1 milligram or less can be employed. Examples of such balances are the Mettler PM 480 and Mettler PC 440 (Mettler Instrument Corp; Hightstown N.J.).

After determining the weight of the wet sample (Ww), it is placed between 2 fine plastic mesh screens on top of 4 disposable paper towels. The sample is squeezed 3 times by firmly rolling a plastic roller over the top screen. The sample is then removed, soaked in distilled water for approximately 2 minutes, and squeezed between mesh screens as before. It is then placed between 8 layers of disposable paper towels (4 on each side) and pressed with 20,000 lbs. of force in a Carver Laboratory Press. The sample is then removed from the paper towels, dried in an oven at 82° C. for 20 minutes, and its dry weight recorded (Wd).

The free absorbent capacity (FAC) is the wet weight (Ww), less the dry weight (Wd) divided by the dry weight (Wd), i.e., FAC=[(Ww−Wd)/Wd]. Another means suitable for obtaining this value is the VWC at 0 cm described supra.

E. Capillary Collapse Pressure

Capillary Collapse Pressure (CCP) is the height (e.g., in cm) at which the vertically hung sample of test material collapses to 50% of its original dimensions due to capillary pressure. This may be obtained using the VWC method described above. The CCP may also be measured as the point at which the foam has 50% of its capacity in the CAH test supra. These techniques are interchangeable. Another means for determining the CCP is to measure the Yield Stress as described infra. The yield stress (YS) is related to the CCP by the following empirical equation: CCP=28.2× YS+1.5 when YS is measured in unit of pounds per square inch. Thus, for example, a foam having a YS=1.1 psi will have a projected CCP of 32.5 cm, which correlates with the measured value. Other techniques may be more convenient and still be suitable for measuring this parameter on the materials of the present invention.

F. Yield Stress

Yield stress is measured on pieces of foam stamped into cylindrical pieces 2.5 cm in diameter and 3–7 mm in thickness. Yield stress is determined from a stress-strain experiment performed on a Rheometrics RSA-II Dynamic Mechanical Analyzer. The experiment is performed at 31° C. (the test sample being equilibrated at this temperature for at least 5 minutes) and at a constant strain rate of 0.1%/second for 600 seconds in compression and 600 seconds in expansion. The instrument records and displays the stress applied to the sample to effect this strain. The yield stress is calculated from the line fit of the initial linear elastic portion of the stress-strain curve intersecting with a line fit of the intermediate plateau region of the stress-strain curve. The stress of the line fit intersection is the yield stress of the sample.

VI. Representative Examples

Figure 5A:
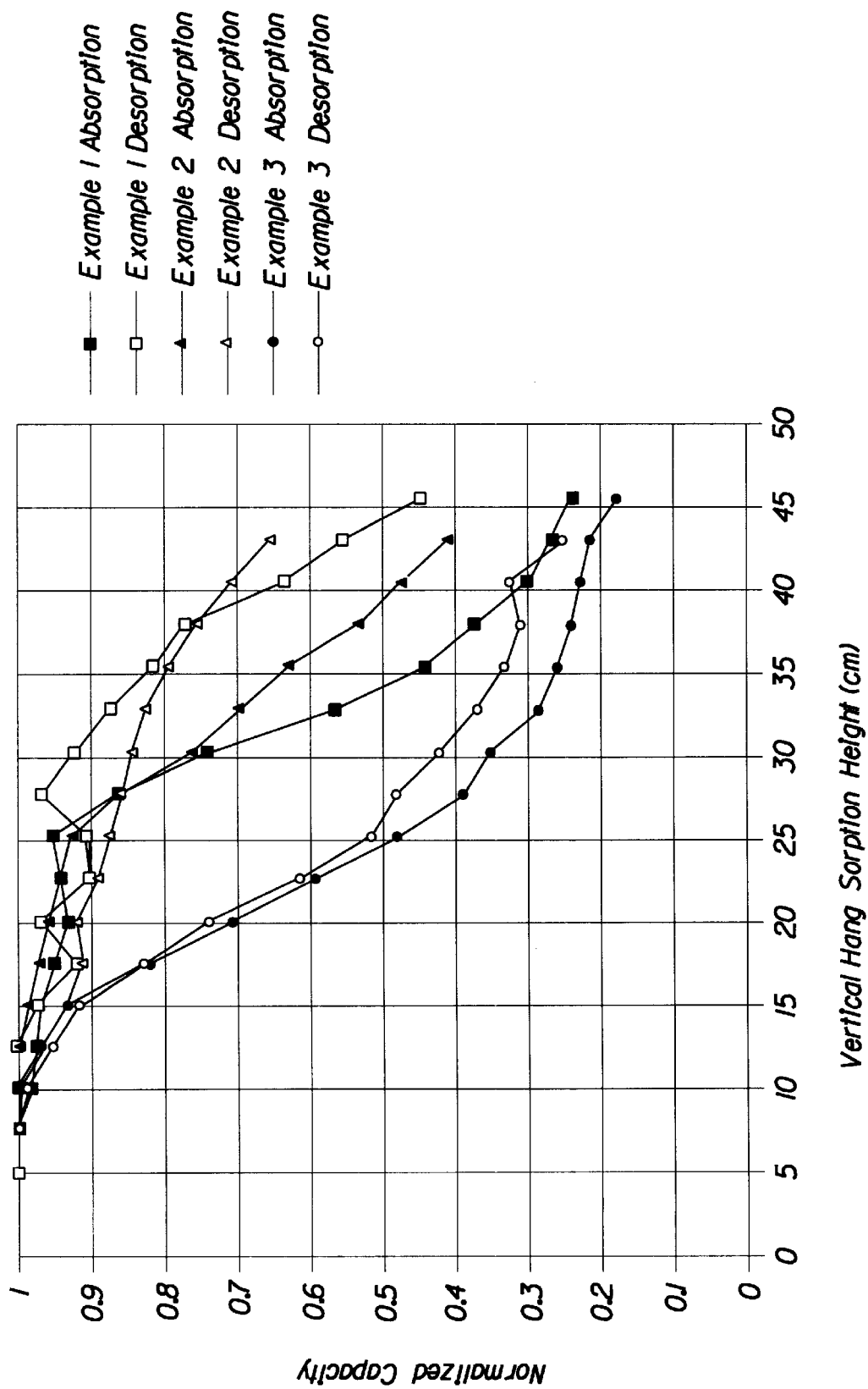
FIGS. 5a and 5b of the drawings are graphical plots showing liquid obtaining (absorption pressure) and liquid holding (desorption pressure) properties of several distribution materials of the present invention.
Figure 5B:
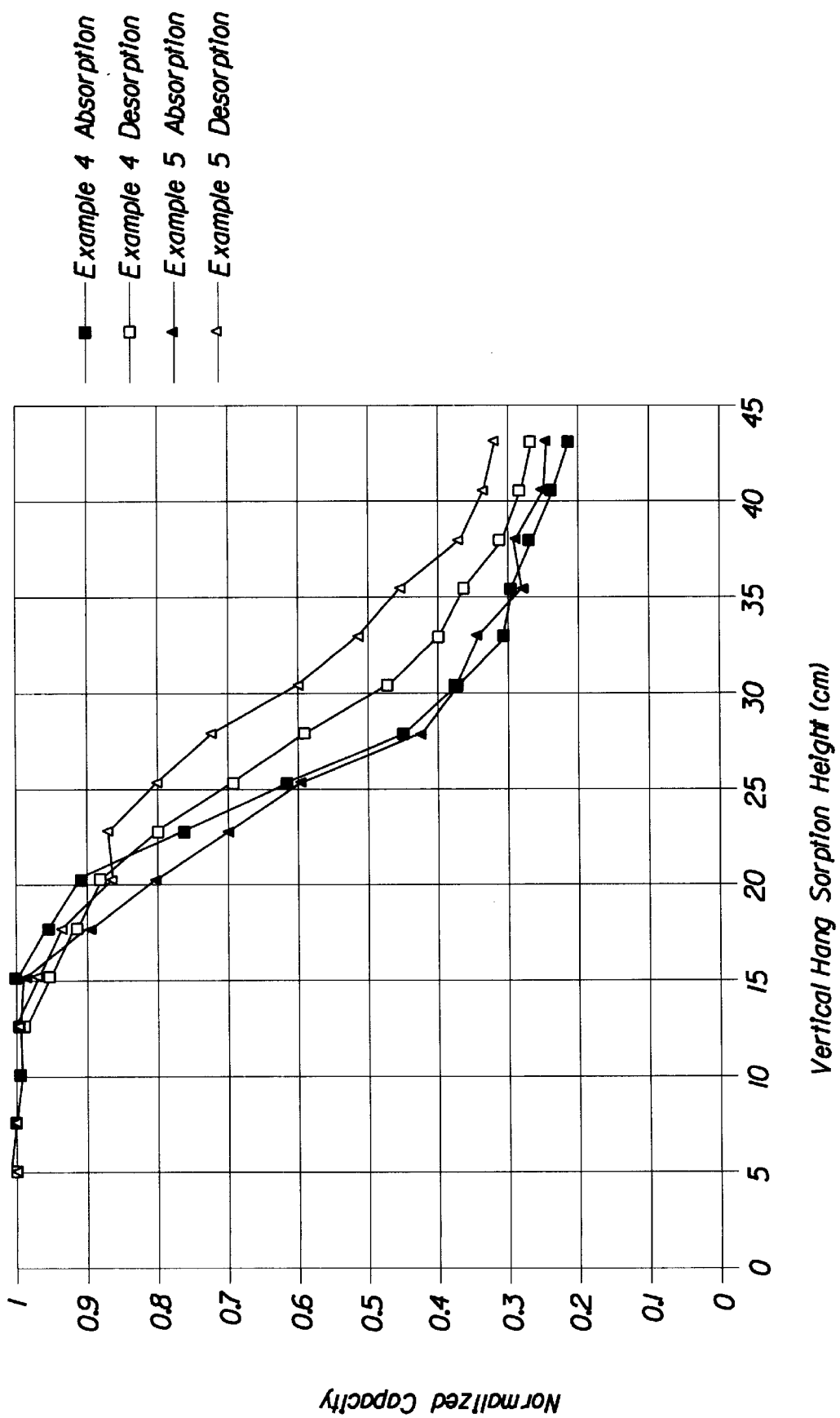

These examples illustrate the specific preparation of collapsed HIPE foams according the present invention. Physical properties of the prepared foams are summarized in Table 1 below. In addition, absorption and desorption curves for these foams are shown graphically in FIGS. 5a and 5b. (The curves are normalized by dividing a foam's capillary absorption and desorption pressures at a given height by the foam's free absorbent capacity (i.e., capacity at 0 cm).) As can be seen from the data in Table 1 and the graph of FIGS. 5a and 5b, each of the distribution materials of the present invention exhibits a CDH:CAH ratio of not more than 1.8, which demonstrates the surprising reduction in hysteresis demonstrated by the distribution materials of the present invention.

A) General Preparation of HIPEs

HIPEs are prepared as described generally in the Examples section of U.S. Pat. No. 5,563,179, supra. Generally, this process comprises appropriate mixing of an aqueous phase containing selected salts with an oil phase containing selected monomers and emulsifiers. The aqueous phase typically contains an initiator such as potassium persulfate and inorganic salt such as calcium chloride. The oil phase typically contains a blend of monomers such as 2-ethylhexylacrylate and crosslinking monomers such as divinyl benzene (which contains ethyl styrene as an impurity) and 1,6-hexanedioldiacrylate. Adjuvants such as antioxidants, opacifying agents, pigments, dyes, fillers, and other generally unreactive chemicals, can also be added to either phase.

The separate streams of the oil phase and water phase (typically heated to between about 30° and about 90° C.) are fed to a dynamic mixing apparatus. Thorough mixing of the combined streams in the dynamic mixing apparatus is achieved by means of a pin impeller. The ratio of the aqueous phase and the oil phase, referred to as the "water-to-oil ratio", or W:O, is used to control the density of the ultimate foam produced. A detailed description of the apparatus and the procedures for establishing the initial HIPE formation is described in more detail in the Examples section of U.S. Pat. No. 5,563,179, supra.

Once the apparatus set-up is filled, agitation is begun in the dynamic mixer, with the impeller turning at a specified RPM. The flow rate of the water phase is then steadily increased to a rate of 44.1 cc/sec in a time period of about 30 sec. and the oil phase flow rate is reduced to 1.25 g/sec over a time period of about 1 min. The back pressure created by the dynamic and static mixers at this point is typically between about 3 and about 8 PSI (about 21 to about 55 kPa). The impeller speed is then adjusted to the desired RPM over a period of 120 sec. The system back pressure responds to this adjustment and remains constant thereafter.

B) Polymerization/Curing of HIPE

The HIPE from the static mixer is collected in a round polypropylene tub, 17 in. (43 cm) in. diameter and 7.5 in. (10 cm) high, with a concentric insert made of Celcon plastic. The insert is 5.0 in. (12.7 cm) in diameter at its base and 4.75 in. (12 cm) in diameter at its top and is 6.75 in. (17.1 cm) high. The HIPE-containing tubs are kept in a room maintained at 65° C. for 18 hours to cure and provide a polymeric HIPE foam.

C) Foam Washing and Dewatering

The cured HIPE foam is removed from the tubs. The foam at this point contains residual water phase (containing dissolved emulsifiers, electrolyte, initiator residues, and initiator). The foam is sliced with a sharp reciprocating saw blade into sheets of desired thickness. These sheets are then subjected to compression in a series of 2 porous nip rolls equipped with vacuum which gradually reduces the residual water phase content of the foam to about 2 times (2×) the weight of the polymerized monomers. At this point, the sheets are then resaturated with a 4% $CaCl_2$ solution at 60° C., are squeezed in a series of 3 porous nip rolls equipped with vacuum to a water phase content of about 2×. The $CaCl_2$ content of the foam is between 2 and 10%.

The HIPE foam is then dried in air for about 16 hours or thermally dried continuously. Such drying reduces the moisture content to about 4–20% by weight of polymerized material.

EXAMPLE 1

Preparation of Distribution Foam from a HIPE

A) HIPE Preparation

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (39% divinylbenzene and 61% ethyl styrene) (2640 g), 2-ethylhexyl acrylate (4720 g), and hexanedioldiacrylate (640 g) is added a diglycerol monooleate emulsifier (480 g), ditallow dimethyl ammonium methyl suflate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (53°–55° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 60° to its neighboring level with each level separated by 0.03 mm, each pin having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure in co-pending U.S. patent application Ser. No. 08/716,510 (T. A. DesMarais), filed Sep. 17, 1996, which issued on Oct. 27, 1998 as U.S. Pat. No. 5,827,909 (herein incorporated by reference). The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 100-812) has 12 elements with a 1 inch (2.5 cm) outside diameter. A hose is mounted downstream from the static mixer to facilitate delivery of the emulsion to the device used for curing. Optionally an additional static mixer is used to provide addition back pressure to keep the hose filled. The optional static mixer can be a 1 inch (2.5 cm) pipe, 12 element mixer (McMaster-Carr Model 3529K53).

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 cc/sec water phase.

Once the apparatus set-up is filled, agitation is begun in the dynamic mixer, with the impeller turning at 850 RPM and recirculation is begun at a rate of about 30 cc/sec. The flow rate of the water phase is then steadily increased to a rate of 151.3 cc/sec over a time period of about 1 min., and the oil phase flow rate is reduced to 2.52 g/sec over a time period of about 3 min. The recirculation rate is steadily increased to about 150 cc/sec during the latter time period. The back pressure created by the dynamic zone and static mixers at this point is about 4.9 PSI (33.8 kPa), which represents the total pressure drop of the system. The Waukesha pump speed is then steadily decreased to a yield a recirculation rate of about 75 cc/sec.

B) Polymerization of HIPE

The HIPE flowing from the static mixer at this point is collected in a round polyethylene tub, 40 in. (102 cm) in diameter and 12.5 in (31.8 cm) high, with removable sides, much like a springform pan used in cooking cakes. A pipe-like polyethylene insert 12.5 in (31.8 cm) in diameter at its base is firmly affixed to the center of the base and is 12.5 in (31.8 cm) high. The HIPE-containing tubs are kept in a room maintained at 65° C. for 18 hours to bring about polymerization and form the foam.

C) Foam Washing and Dewatering

The cured HIPE foam is removed from the curing tubs. The foam at this point has residual water phase (containing dissolved emulsifiers, electrolyte, initiator residues, and initiator) about 55–65 times (55–65×) the weight of polymerized monomers. The foam is sliced with a sharp reciprocating saw blade into sheets which are 0.2 inches (5.1 mm) in thickness. These sheets are then subjected to compression in a series of 2 porous nip rolls equipped with vacuum which gradually reduce the residual water phase content of the foam to about 3 times (3×) the weight of the polymerized material. At this point, the sheets are then resaturated with a 4% CaCl$_2$ solution at 60° C., are squeezed in a series of 3 porous nip rolls equipped with vacuum to a water phase content of about 1.5–2×. The CaCl$_2$ content of the foam is between 6 and 10%.

The foam remains compressed after the final nip at a thickness of about 0.027 in. (0.069 cm). The foam is then dried in air for about 16 hours. Such drying reduces the moisture content to about 9–17% by weight of polymerized material. At this point, the foam sheets are very drapeable.

EXAMPLE 2

Preparation of Distribution Foam from a HIPE

A) HIPE Preparation

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (640 g), ditallow dimethyl ammonium methyl suflate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (75°–77° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 60° to its neighboring level with each level separated by 0.03 mm, each pin having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure in co-pending U.S. patent application Ser. No. 08/716,510 (T. A. DesMarais), filed Sep. 17, 1996, which issued on Oct. 27, 1998 as U.S. Pat. No. 5,827,909 (herein incorporated by reference). The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 101-212) normally has 12 elements with a 1.5 inch (3.8 cm) outside diameter, but 7 inches (17.8 cm) were removed to fit in the equipment space. A hose is mounted downstream from the static mixer to facilitate delivery of the emulsion to the device used for curing. Optionally an additional static mixer is used to provide addition back pressure to keep the hose filled. The optional static mixer can be the same as the first without modification.

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 cc/sec water phase.

Once the apparatus set-up is filled, agitation is begun in the dynamic mixer, with the impeller turning at 800 RPM and recirculation is begun at a rate of about 30 cc/sec. The flow rate of the water phase is then steadily increased to a rate of 151.3 cc/sec over a time period of about 1 min., and the oil phase flow rate is reduced to 2.52 g/sec over a time period of about 3 min. The recirculation rate is steadily increased to about 150 cc/sec during the latter time period. The back pressure created by the dynamic zone and static mixers at this point is about 4.2 PSI (29 kPa), which represents the total pressure drop of the system.

B) Polymerization of HIPE

The HIPE flowing from the static mixer at this point is collected in a round polyethylene tub, 40 in. (102 cm) in diameter and 12.5 in (31.8 cm) high, with removable sides, much like a springform pan used in cooking cakes. A pipe-like polyethylene insert 12.5 in (31.8 cm) in diameter at its base is firmly affixed to the center of the base and is 12.5 in (31.8 cm) high. The HIPE-containing tubs are kept in a room maintained at 65° C. for 18 hours to bring about polymerization and form the foam.

C) Foam Washing and Dewatering

The cured HIPE foam is removed from the curing tubs. The foam at this point has residual water phase (containing dissolved emulsifiers, electrolyte, initiator residues, and initiator) about 58–62 times (58–62×) the weight of polymerized monomers. The foam is sliced with a sharp reciprocating saw blade into sheets which are 0.2 inches (5.1 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% CaCl$_2$ solution at 60° C., are squeezed in a series of 3 porous nip rolls equipped with vacuum to a water phase content of about 2×. The CaCl$_2$ content of the foam is between 3 and 6%.

The foam remains compressed after the final nip at a thickness of about 0.047 in. (0.071 cm). The foam is then dried in air for about 16 hours. Such drying reduces the moisture content to about 9–17% by weight of polymerized material. At this point, the foam sheets are very drapeable.

EXAMPLE 3

Preparation of Distribution Foam from a HIPE

A) HIPE Preparation

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (640 g), ditallow dimethyl ammonium methyl suflate (80 g), and Tinuvin 765 (40 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (75°–77° C.) are fed to a dynamic mixing apparatus. Thorough mixing of the combined streams in the dynamic mixing apparatus is achieved by means of a pin impeller. The pin impeller comprises a cylindrical shaft of about 21.6 cm in length with a diameter of about 1.9 cm. The shaft holds 6 rows of pins, one level with 3 rows having 21 pins and another level with 3 rows having 21 pins, each of the three pins at each level disposed at an angle of 120° to each other, with the next level down disposed at 60° to its neighboring level with each level separated by 0.03 mm, each having a diameter of 0.5 cm extending outwardly from the central axis of the shaft to a length of 1.4 cm. The pin impeller is mounted in a cylindrical sleeve which forms the dynamic mixing apparatus, and the pins have a clearance of 3 mm from the walls of the cylindrical sleeve.

A minor portion of the effluent exiting the dynamic mixing apparatus is withdrawn and enters a recirculation zone, as shown in the Figure in co-pending U.S. patent application Ser. No. 08/716,510 (T. A. DesMarais), filed Sep. 17, 1996, which issued on Oct. 27, 1998 as U.S. Pat. No. 5,827,909 (herein incorporated by reference). The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 070-821), modified by cutting off 2.4 inches (6.1 cm) of its original length) is 14 inches (35.6 cm) long with a 0.5 inch (1.3 cm) outside diameter.

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 1.89 g/sec oil phase and 7.56 cc/sec water phase.

Once the apparatus set-up is filled, agitation is begun in the dynamic mixer, with the impeller turning at 1000 RPM and recirculation is begun at a rate of about 8 cc/sec. The flow rate of the water phase is then steadily increased to a rate of 45.4 cc/sec over a time period of about 1 min., and the oil phase flow rate is reduced to 0.6 g/sec over a time period of about 3 min. The recirculation rate is steadily increased to about 45 cc/sec during the latter time period. The back pressure created by the dynamic zone and static mixers at this point is about 2.9 PSI (20 kPa), which represents the total pressure drop of the system.

B) Polymerization of HIPE

The HIPE flowing from the static mixer at this point is collected in a round polypropylene tub, 17 in. (43 cm) in diameter and 7.5 in (10 cm) high, with a concentric insert made of Celcon® plastic. The insert is 5 in (12.7 cm) in diameter at its base and 4.75 in (12 cm) in diameter at its top and is 6.75 in (17.1 cm) high. The HIPE-containing tubs are kept in a room maintained at 65° C. for 18 hours to bring about polymerization and form the foam.

C) Foam Washing and Dewatering

The cured HIPE foam is removed from the curing tubs. The foam at this point has residual water phase (containing dissolved emulsifiers, electrolyte, initiator residues, and initiator) about 70–80 times (70–80×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 3 times (3×) the weight of the polymerized material. At this point, the sheets are s then resaturated with a 1.5% $CaCl_2$ solution at 60° C., are squeezed in a series of 3 porous nip rolls equipped with vacuum to a water phase content of about 2×. The $CaCl_2$ content of the foam is between 3 and 5%.

The foam remains compressed after the final nip at a thickness of about 0.031 in. (0.079 cm). The foam is then dried in air for about 16 hours. Such drying reduces the moisture content to about 9–17% by weight of polymerized material. At this point, the foam sheets are very drapeable.

EXAMPLES 4 AND 5

Preparation of Distribution Foams from a HIPE

A) HIPE Preparation

Anhydrous calcium chloride (22.73 kg) and potassium persulfate (284 g) are dissolved in 567 liters of water. This provides the water phase stream to be used in a continuous process for forming a HIPE emulsion.

To a monomer combination comprising divinylbenzene (42.5% divinylbenzene and 57.5% ethyl styrene) (2464 g), 2-ethylhexyl acrylate (5056 g), and hexanedioldiacrylate (640 g) is added a diglycerol monooleate emulsifier (480 g), ditallow dimethyl ammonium methyl suflate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (53°–55° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 60° to its neighboring level with each level separated by 0.03 mm, each pin having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure in co-pending U.S. patent application Ser. No. 08/716,510 (T. A. DesMarais), filed Sep. 17, 1996, which issued on Oct. 27, 1998 as U.S. Pat. No. 5,827,909 (herein incorporated by reference). The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 100-812) has 12 elements with a 1 inch (2.5 cm) outside diameter. A hose is mounted downstream from the static mixer to facilitate delivery of the emulsion to the device used for curing. Optionally an additional static mixer is used to provide addition back pressure to keep the hose filled. The optional static mixer can be a 1 inch (2.5 cm) pipe, 12 element mixer (McMaster-Carr Model 3529K53).

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 cc/sec water phase.

Once the apparatus set-up is filled, agitation is begun in the dynamic mixer, with the impeller turning at 500 RPM (for the foam of Example 4) and recirculation is begun at a rate of about 30 cc/sec. The flow rate of the water phase is then steadily increased to a rate of 151.3 cc/sec over a time period of about 1 min., and the oil phase flow rate is reduced to 2.52 g/sec over a time period of about 3 min. The recirculation rate is steadily increased to about 150 cc/sec during the latter time period. The back pressure created by the dynamic zone and static mixers at this point is about 4.0 PSI (27.6 kPa), which represents the total pressure drop of the system. The Waukesha pump speed is then steadily decreased to a yield a recirculation rate of about 75 cc/sec. The foam of Example 5 is prepared in the same manner, except by increasing the impeller RPM to 600, at which point the back pressure created by the dynamic zone and the static mixers is about 4.3 PSI (29.7 kPa). The steps that follow are performed on the HIPEs of Examples 4 and 5.

B) Polymerization of HIPE

The HIPE flowing from the static mixer at this point is collected in a round polyethylene tub, 40 in. (102 cm) in diameter and 12.5 in (31.8 cm) high, with removable sides, much like a springform pan used in cooking cakes. A pipe-like polyethylene insert 12.5 in (31.8 cm) in diameter at its base is firmly affixed to the center of the base and is 12.5 in (31.8 cm) high. The HIPE-containing tubs are kept in a room maintained at 65° C. for 18 hours to bring about polymerization and form the foam.

C) Foam Washing and Dewatering

The cured HIPE foam is removed from the curing tubs. The foam at this point has residual water phase (containing dissolved emulsifiers, electrolyte, initiator residues, and initiator) about 55–65 times (55–65×) the weight of polymerized monomers. The foam is is sliced with a sharp reciprocating saw blade into sheets which are 0.2 inches (5.1 mm) in thickness. These sheets are then subjected to compression in a series of 2 porous nip rolls equipped with vacuum which gradually reduce the residual water phase content of the foam to about 3 times (3×) the weight of the polymerized material. At this point, the sheets are then resaturated with a 4% $CaCl_2$ solution at 60° C., are squeezed in a series of 3 porous nip rolls equipped with vacuum to a water phase content of about 1.5–2×. The $CaCl_2$ content of the foam is between 6 and 10%.

The foam remains compressed after the final nip at a thickness of about 0.027 in. (0.069 cm). The foam is then dried in air for about 16 hours. Such drying reduces the moisture content to about 9–17% by weight of polymerized material. At this point, the foam sheets are very drapeable.

TABLE 1

Summary of Measured Data on Foams.

| Foam | FAC* (g/g) | VWC* (g/g) at 15 cm | CAH* (cm) | CDH* (cm) | CDH:CAH Ratio | Wicking Time (min. to 15 cm) | Yield Stress (kPa) |
| --- | --- | --- | --- | --- | --- | --- | --- |
| Example 1 | 58 | 56 | 34 | 44 | 1.3 | 15 | 3.0 |
| Example 2 | 58 | 55 | 40 | 48 | 1.2 | 15 | 3.0 |
| Example 3 | 70 | 64 | 25 | 27 | 1.1 | 13 | 1.5 |
| Example 4 | 58 | 55 | 27 | 29 | 1.1 | 7 | 1.5 |
| Example 5 | 58 | 56 | 27 | 33 | 1.2 | 8 | 1.5 |

*FAC = Free Absorbent Capacity, g aqueous liquid per g dry material;
VWC = Vertical Wicking Capacity, g aqueous liquid per g dry material;
CAH = Capillary Absorption Height;
CDH = Capillary Desorption Height.

What is claimed is:

1. A material capable of distributing aqueous liquids, the material having:
    A) a ratio of capillary desorption height to capillary absorption height of not more than about 1.8:1;
    B) a capillary desorption height of not more than about 50 cm;
    C) the ability to wick synthetic urine at 31° C. to a height of 15 cm in not more than about 25 minutes; and
    D) a vertical wicking capacity at 10 cm of at least about 10 g/g.

2. The material of claim 1 having a ratio of capillary desorption height to capillary absorption height of not more than about 1.6:1.

3. The material of claim 2 having a ratio of capillary desorption height to capillary absorption height of not more than about 1.4:1.

4. The material of claim 3 having a ratio of capillary desorption height to capillary absorption height of not more than about 1.2:1.

5. The material of claim 4 having a ratio of capillary desorption height to capillary absorption height of not more than about 1.1:1.

6. The material of claim 1 having a capillary desorption height of not more than about 45 cm.

7. The material of claim 6 having a capillary desorption height of not more than about 40 cm.

8. The material of claim 1 having a capillary absorption height of at least about 15 cm.

9. The material of claim 1 having the ability to wick synthetic urine at 31° C. to a height of 15 cm in not more than about 20 minutes.

10. The material of claim 9 having the ability to wick synthetic urine at 31° C. to a height of 15 cm in not more than about 10 minutes.

11. The material of claim 1 having a vertical wicking capacity at 15 cm of at least about 6 g/g.

12. The material of claim 11 having a vertical wicking capacity at 15 cm of at least about 7 g/g.

13. The material of claim 1 having a free absorbent capacity of at least about 15 g/g.

14. The material of claim 1 having:
   A) a ratio of capillary desorption height to capillary absorption height of not more than about 1.6:1;
   B) a capillary desorption height of not more than about 45 cm;
   C) the ability to wick synthetic urine at 31° C. to a height of 15 cm in not more than about 20 minutes; and
   D) a vertical wicking capacity at 15 cm of at least about 7 g/g.

15. An absorbent article comprising a topsheet, a backsheet and an absorbent core positioned between the topsheet and the backsheet; wherein the absorbent core comprises the material of claim 14.

16. An absorbent article comprising a topsheet, a backsheet and an absorbent core positioned between the topsheet and the backsheet; wherein the absorbent core comprises the material of claim 1.

17. A material capable of distributing aqueous liquids, the material having:
   A) a ratio of capillary desorption height to capillary absorption height of not more than about 1.5:1;
   B) a capillary desorption height of not more than about 40 cm;
   C) the ability to wick synthetic urine at 31° C. to a height of 15 cm in not more than about 20 minutes; and
   D) a vertical wicking capacity at 15 cm of at least about 9 g/g.

18. An absorbent article comprising a topsheet, a backsheet and an absorbent core positioned between the topsheet and the backsheet; wherein the absorbent core comprises the material of claim 17.

19. A material capable of distributing aqueous liquids, wherein the material is a hydrophilic, flexible polymeric foam structure of interconnected open-cells having:
   A) a ratio of capillary desorption height to capillary absorption height of not more than about 1.8:1;
   B) a capillary desorption height of not more than about 50 cm;
   C) the ability to wick synthetic urine at 31° C. to a height of 15 cm in not more than about 25 minutes; and
   D) a vertical wicking capacity at 15 cm of at least about 6 g/g.

20. The foam material of claim 19 having a ratio of capillary desorption height to capillary absorption height of not more than about 1.6:1.

21. The foam material of claim 20 having a ratio of capillary desorption height to capillary absorption height of not more than about 1.4:1.

22. The foam material of claim 21 having a ratio of capillary desorption height to capillary absorption height of not more than about 1.2:1.

23. The foam material of claim 22 having a ratio of capillary desorption height to capillary absorption height of not more than about 1.1:1.

24. The foam material of claim 19 having a capillary desorption height of not more than about 45 cm.

25. The foam material of claim 24 having a capillary desorption height of not more than about 40 cm.

26. The foam material of claim 19 having a capillary absorption height of at least about 15 cm.

27. The foam material of claim 19 having the ability to wick synthetic urine at 31° C. to a height of 15 cm in not more than about 20 minutes.

28. The foam material of claim 27 having the ability to wick synthetic urine at 31° C. to a height of 15 cm in not more than about 10 minutes.

29. The foam material of claim 19 having a vertical wicking capacity at 15 cm of at least about 6 g/g.

30. The foam material of claim 29 having a vertical wicking capacity at 15 cm of at least about 7 g/g.

31. The foam material of claim 19 having a free absorbent capacity of at least about 15 g/g.

32. The foam material of claim 19 having:
   A) a ratio of capillary desorption height to capillary absorption height of not more than about 1.6:1;
   B) a capillary desorption height of not more than about 45 cm;
   C) the ability to wick synthetic urine at 31° C. to a height of 15 cm in not more than about 20 minutes; and
   D) a vertical wicking capacity at 15 cm of at least about 7 g/g.

33. An absorbent article comprising a topsheet, a backsheet and an absorbent core positioned between the topsheet and the backsheet; wherein the absorbent core comprises the material of claim 32.

34. The foam material of claim 19 having a capillary collapse pressure of at least about 15 cm.

35. The foam material of claim 34 having a capillary collapse pressure of at least about 20 cm.

36. An absorbent article comprising a topsheet, a backsheet and an absorbent core positioned between the topsheet and the backsheet; wherein the absorbent core comprises the material of claim 19.

37. A material capable of distributing aqueous liquids, wherein the material is a hydrophilic, flexible polymeric foam structure of interconnected open-cells having:
   A) a ratio of capillary desorption height to capillary absorption height of not more than about 1.5:1;
   B) a capillary desorption height of not more than about 40 cm;
   C) the ability to wick synthetic urine at 31° C. to a height of 15 cm in not more than about 25 minutes; and
   D) a vertical wicking capacity at 15 cm of at least about 9 g/g.

38. An absorbent article comprising a topsheet, a backsheet and an absorbent core positioned between the topsheet and the backsheet; wherein the absorbent core comprises the material of claim 37.

* * * * *

UNITED STATES PATENT AND TRADEMARK OFFICE
CERTIFICATE OF CORRECTION

PATENT NO. : 6,013,589  
DATED : January 11, 2000  
INVENTOR(S) : DesMarais et al.

Page 1 of 1

It is certified that error appears in the above-identified patent and that said Letters Patent is hereby corrected as shown below:

Column 18,
Line 35, please delete "egde" and insert therefor -- edge --.

Column 30,
Line 16, after "are" please delete "s".

Column 32,
Line 9, please delete one "is".

Signed and Sealed this

Twenty-sixth Day of November, 2002

Attest:

Attesting Officer

JAMES E. ROGAN
Director of the United States Patent and Trademark Office